(12) United States Patent
Triplett et al.

(10) Patent No.: US 9,877,748 B2
(45) Date of Patent: *Jan. 30, 2018

(54) SYSTEM AND METHOD FOR MULTIPLE LEVEL FACET JOINT ARTHROPLASTY AND FUSION

(71) Applicant: GLOBUS MEDICAL, INC., Audubon, PA (US)

(72) Inventors: Daniel J. Triplett, Providence, UT (US); Alan Chervitz, Palm Harbor, FL (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/236,962

(22) Filed: Aug. 15, 2016

(65) Prior Publication Data

US 2016/0346015 A1   Dec. 1, 2016

Related U.S. Application Data

(60) Continuation of application No. 14/291,297, filed on May 30, 2014, now Pat. No. 9,439,688, which is a continuation of application No. 12/240,512, filed on Sep. 29, 2008, now Pat. No. 8,777,994, which is a division of application No. 11/463,513, filed on Aug. 9, 2006, now Pat. No. 8,562,649.

(60) Provisional application No. 60/760,863, filed on Jan. 19, 2006.

(51) Int. Cl.
*A61B 17/70* (2006.01)
*A61B 17/17* (2006.01)
*A61F 2/44* (2006.01)
*A61F 2/30* (2006.01)

(52) U.S. Cl.
CPC ...... *A61B 17/7064* (2013.01); *A61B 17/1757* (2013.01); *A61B 17/704* (2013.01); *A61B 17/7032* (2013.01); *A61B 17/7035* (2013.01); *A61B 17/7043* (2013.01); *A61F 2/4405* (2013.01); *A61F 2002/30507* (2013.01); *A61F 2002/30649* (2013.01); *A61F 2002/448* (2013.01); *A61F 2220/0025* (2013.01)

(58) Field of Classification Search
CPC ............ A61B 17/7062; A61B 17/7064; A61B 17/7007; A61B 17/7008; A61F 2/4405
See application file for complete search history.

(56) References Cited

U.S. PATENT DOCUMENTS

| | | | | |
|---|---|---|---|---|
| 2005/0273133 | A1* | 12/2005 | Shluzas | A61B 17/3439 606/198 |
| 2006/0009766 | A1* | 1/2006 | Lee | A61B 17/7052 74/1 R |
| 2006/0052785 | A1* | 3/2006 | Augostino | A61B 17/7049 606/247 |

* cited by examiner

Primary Examiner — Julianna N Harvey

(57) ABSTRACT

Facet joint replacement implants may be designed for use on multiple adjacent vertebral levels. Each superior implant may have a substantially semispherical concave surface, and each inferior implant may have a cooperating semispherical convex surface that is deformable to enable it to be pressed into the superior implant concave surface to fix the relative orientations of the superior and inferior implants. Thus, the inferior implant may be attached to the same pedicle as the superior implant, but may also be oriented independently of the superior implant and then fixed in position. Similar mounting structures may be used to attach one or more fusion implants to a level adjacent to that of a facet joint replacement implant.

20 Claims, 18 Drawing Sheets

SYSTEM AND METHOD FOR MULTIPLE LEVEL FACET JOINT ARTHROPLASTY AND FUSION

CROSS REFERENCE TO RELATED APPLICATIONS

This application is a continuation of U.S. Ser. No. 14/291,297, filed May 30, 2014, which is a continuation of U.S. Ser. No. 12/240,512, filed Sep. 29, 2008, which is a divisional of the following:

U.S. application Ser. No. 11/463,513, filed Aug. 9, 2006, now issued as U.S. Pat. No. 8,562,649, and is entitled SYSTEM AND METHOD FOR MULTIPLE LEVEL FACET JOINT ARTHROPLASTY AND FUSION, which claims the benefit of the following U.S. Application No. 60/760,863, filed Jan. 19, 2006, and is entitled MULTI-LEVEL FACET ARTHROPLASTY WITH ADJACENT LEVEL FUSION. All of these references are incorporated herein by reference in their entireties.

The following documents are also incorporated herein by reference in their entireties:

U.S. application Ser. No. 10/687,856, filed Oct. 17, 2003, and is entitled FACET JOINT REPLACEMENT;

U.S. application Ser. No. 10/860,778, filed Jun. 2, 2004, and is entitled SPINAL FACET IMPLANT WITH SPHERICAL IMPLANT APPOSITION SURFACE AND BONE BED AND METHODS OF USE;

U.S. application Ser. No. 10/860,543, filed Jun. 2, 2004, and is entitled SPINAL FACET IMPLANTS WITH MATING ARTICULATING BEARING SURFACE AND METHODS OF USE;

U.S. application Ser. No. 10/860,495, filed Jun. 2, 2004, and is entitled LINKED BILATERAL SPINAL FACET SUPERIOR AND INFERIOR IMPLANTS AND METHODS OF USE;

U.S. application Ser. No. 10/860,487, filed Jun. 2, 2004, and is entitled SPINAL FACET JOINT IMPLANT;

U.S. application Ser. No. 10/990,191, filed Nov. 15, 2004, and is entitled SURGICAL MEASUREMENT AND RESECTION FRAMEWORK;

U.S. application Ser. No. 10/989,971, filed Nov. 15, 2004, and is entitled SURGICAL MEASUREMENT SYSTEMS AND METHODS;

U.S. application Ser. No. 11/063,941, filed Feb. 22, 2005, and is entitled POLYAXIAL ORTHOPEDIC FASTENING APPARATUS;

U.S. application Ser. No. 11/388,389, filed Mar. 24, 2006, and is entitled POLYAXIAL REAMING APPARATUS AND METHOD;

U.S. application Ser. No. 11/312,323, filed Feb. 22, 2005, and is entitled POLYAXIAL ORTHOPEDIC FASTENING APPARATUS WITH INDEPENDENT LOCKING MODES;

U.S. Application No. 60/757,592, filed Jan. 9, 2006, and is entitled AFR SURGICAL INSTRUMENTATION AND TECHNIQUE; and U.S. application Ser. No. 11/350,179, filed Feb. 7, 2006, and is entitled FACET JOINT IMPLANT CROSSLINKING APPARATUS AND METHOD.

BACKGROUND OF THE INVENTION

1. The Field of the Invention

The present invention relates generally to orthopedic implants and associated methods, and more particularly, to facet joint replacement implants and methods.

2. The Relevant Technology

Many people experience back pain. Back pain is not only uncomfortable, but can be particularly debilitating. Many people who wish to participate in sports, manual labor, or even sedentary employment are unable to do so because of pains that arise from motion of or pressure on the spinal column. Such pains are often caused by traumatic, inflammatory, metabolic, synovial, neoplastic and degenerative disorders of the spine.

In order to alleviate such injuries and pains, spinal fusion techniques have been used for many years to essentially lock two vertebrae together. More recently, artificial discs have been used to replace natural intervertebral discs to correct disc pathologies, while still permitting the adjacent vertebrae to move with respect to each other. Various implants have also been proposed for the partial or complete replacement of vertebral facet joints to alleviate discomfort associated with diseased or atrophied articular processes, while still permitting intervertebral motion.

One deficiency in many of the proposed implants and methods is that they only permit the replacement of articular surfaces on a single vertebral level (i.e., a single "facet joint"). Many known devices are attached to a vertebra in such a manner that a similar device for an adjacent level cannot be attached to the same vertebra. Accordingly, facet joint pathologies that extend along multiple joints cannot effectively be corrected.

Another deficiency in many of the proposed implants and methods is that, once an implant has been used to replace part or all of a single facet joint, the implant interferes with the use of another implant to fuse an adjacent vertebral level. Accordingly, the correction of spinal pathologies extending along multiple vertebral joints is further inhibited.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to facet joint replacement implants that can be applied to multiple adjacent vertebral levels and/or used with adjacent-level fusion implants. The facet joint replacement implants and fusion implants are independently orientable at each vertebral level to compensate for natural variations in spinal morphology.

Figure 1:
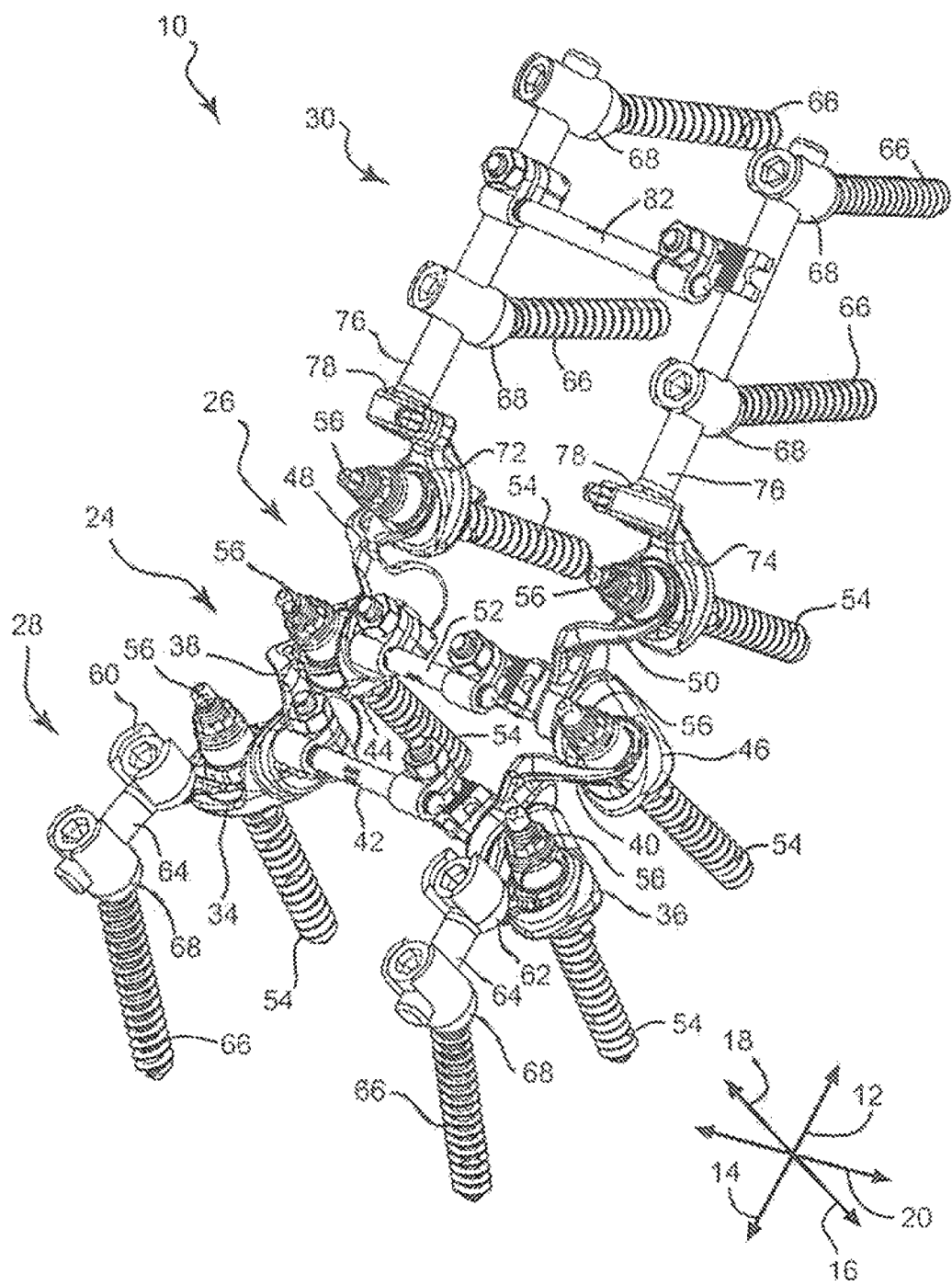
FIG. 1 is a perspective view of a system according to one embodiment of the invention, in which multiple level facet joint replacement may be carried out with adjacent level fusion.

Referring to FIG. 1, a perspective view illustrates a system 10 according to one embodiment of the invention, in which multiple level facet joint replacement may be carried out with adjacent level fusion. The directional arrows of FIG. 1 illustrate how the system 10 would be oriented with respect to a human spine by illustrating a cephalad direction 12, a caudal direction 14, an anterior direction 16, a posterior direction 18, and a medial/lateral direction 20.

The configuration of the system 10 will be explained in the descriptions of FIGS. 1 through 4, and the configuration of an alternative system without adjacent level fusion will be explained in the descriptions of FIGS. 5 through 7. One method of implanting the system 10 and securing it to a portion of a human spine will be shown and described in connection with FIGS. 8 through 16, and implantation of the alternative system will be set forth in the description of FIG. 18.

In the embodiment of FIG. 1, the system 10 includes a caudal facet joint assembly 24, a cephalad facet joint assembly 26, a caudal fusion assembly 28, and a cephalad fusion assembly 30. Each of the facet joint assemblies 24, 26 provides replacement (i.e., arthroplasty) of the facet articular surfaces of one "facet joint," which includes the two superior articular surfaces of one vertebra and the two inferior articular surfaces of a second vertebra superior to the first vertebra. The facet joint assemblies 24, 26 may substantially duplicate the shapes and orientations of the natural articular surfaces so that they provide natural, or "anatomic" articulation that feels to the patient like the natural motion of a healthy spinal joint.

The caudal fusion assembly 28 is designed to substantially immobilize one facet joint by substantially preventing relative motion between two vertebrae. The cephalad fusion assembly 30 is designed to substantially immobilize two facet joints by substantially preventing relative motion between three vertebrae. If desired, the caudal fusion assembly 28 and/or the cephalad fusion assembly 30 may be used on combination with other implants such as intervertebral spacers, fusion cages, anterior plates to enhance the stability and/or fusion of the joints involved. The use of such implants is known in the art; accordingly, they are not described herein.

If desired, the system 10 may be applied to the sacrum and the lumbar vertebrae, such that the caudal fusion assembly 28 immobilizes the joint between S1 and L5, the caudal facet joint assembly 24 provides motion of the joint between L5 and L4, the cephalad facet joint assembly 26 provides motion of the joint between L4 and L3, and the cephalad fusion assembly immobilizes the joint between L3 and L2 and the joint between L2 and L1. However, the present invention is not limited to lumbar/sacral applications, and the implants and techniques illustrated may be readily adapted by one of skill in the art for use with thoracic vertebrae, cervical vertebrae, and/or any combination of spinal vertebrae and the sacrum.

As shown, the caudal facet joint assembly 24 has a left superior prosthesis 34, a right superior prosthesis 36, a left inferior prosthesis 38, and a right inferior prosthesis 40. The superior prostheses 34, 36 are shaped to replace the superior articular surfaces of a vertebra, and the inferior prostheses 38, 40 are shaped to replace the inferior articular surfaces of an adjacent vertebra. Due to natural variations in vertebral articular processes, the superior prostheses 34, 36 need not be mirror images of each other, and the inferior prostheses 38, 40 also need not be mirror images of each other. Rather, each of the prostheses 34, 36, 38, 40 of the caudal facet joint assembly 24 may be selected from a kit of differently-dimensioned prostheses designed for use with a wide variety of vertebral morphologies.

Furthermore, the left and right inferior prostheses 38, 40 may be secured together through the use of a crosslink assembly 42. The crosslink assembly 42 substantially prevents relative motion between the left and right inferior prostheses 38, 40 to ensure that they do not shift under the loads produced by articulation with the superior prostheses 34, 36. The crosslink assembly 42 may be designed to be attachable in loose form to the inferior prostheses 38, 40 so that the prostheses 38, 40 can be reoriented prior to tightening of the crosslink assembly 42 to a rigid state.

As also shown, the cephalad facet joint assembly 26 has a left superior prosthesis 44, a right superior prosthesis 46, a left inferior prosthesis 48, and a right inferior prosthesis 50. The inferior prostheses 48, 50 may be secured together through the use of a crosslink 52. The prostheses 44, 46, 48, 50 and the crosslink 52 of the cephalad facet joint assembly 26 may be configured similarly to the prostheses 34, 36, 38, 40 and the crosslink 42 of the caudal facet joint assembly 24.

However, due to variations in bone structures between adjacent vertebrae, the prostheses 44, 46, 48, 50 and the crosslink 52 need not be identical to the prostheses 34, 36, 38, 40 and the crosslink 42.

The prostheses 34, 36, 38, 40, 44, 46, 48, 50 of the caudal facet joint assembly 24 and the cephalad facet joint assembly 26 may be secured to vertebrae through the use of fixation members, in the form of pedicle screws 54, and locking assemblies 56. The locking assemblies 56 may be used to independently lock out rotational and translational motion of the prostheses 34, 36, 38, 40, 44, 46, 48, 50 relative to the pedicle screws 54. The inferior prostheses 38, 40 of the caudal facet joint assembly 24 may be shaped to nest within the superior prostheses 44, 46 of the cephalad facet joint assembly 26 so that the inferior prostheses 38, 40 and the superior prostheses 44, 46 can be secured to the corresponding vertebra through the use of a single pair of pedicle screws 54 and locking assemblies 56.

The caudal fusion assembly 28 may have a left superior prosthesis 60, a right superior prosthesis 62, and two rods 64. The superior ends of the rods 64 may be secured to the corresponding vertebra via the superior prostheses 60, 62. The inferior ends of the rods 64 may be secured to the immediately inferior vertebra through the use of pedicle screws 66 and yoke assemblies 68. The superior prostheses 60, 62 are shaped to nest within the superior prostheses 34, 36 of the caudal facet joint assembly such that the superior prostheses 60, 62 and the superior prostheses 34, 36 can be secured to the corresponding vertebra with a single pair of pedicle screws 54 and locking assemblies 56.

The cephalad fusion assembly 30 may have a left inferior prosthesis 72, a right inferior prosthesis 74, a pair of rods 76, a pair of polyaxial rod connectors 78, and a crosslink assembly 82. The inferior ends of the rods 76 may be secured to the corresponding vertebra via the inferior prostheses 72, 74. The central portions of the rods 76 and the superior ends of the rods 76 may be secured to the two immediately superior vertebrae through the use of pedicle screws 66 and yoke assemblies 68 like those used in connection with the caudal fusion assembly 28. The crosslink assembly rigidly connects the rods 76 together to maintain the rigidity of the cephalad fusion assembly 30. The inferior prostheses 48, 50 of the cephalad facet joint assembly 26 are shaped to nest within the inferior prostheses 72, 74 of the cephalad fusion assembly 30 such that the inferior prostheses 48, 50 and the inferior prostheses 72, 74 can be secured to the corresponding vertebra with a single pair of pedicle screws 54 and locking assemblies 56.

It will be appreciated by those of skill in the art that the various assemblies 24, 26, 28, 30 can be interchanged in modular fashion and applied in a variety of combinations to treat spinal disorders occurring across multiple joint motion segments. Thus, the specific needs of the patient can be accurately addressed. Fusion and facet joint replacement can be applied to adjacent or non-adjacent vertebral levels, or either fusion or facet joint replacement can be exclusively utilized.

Figure 2:
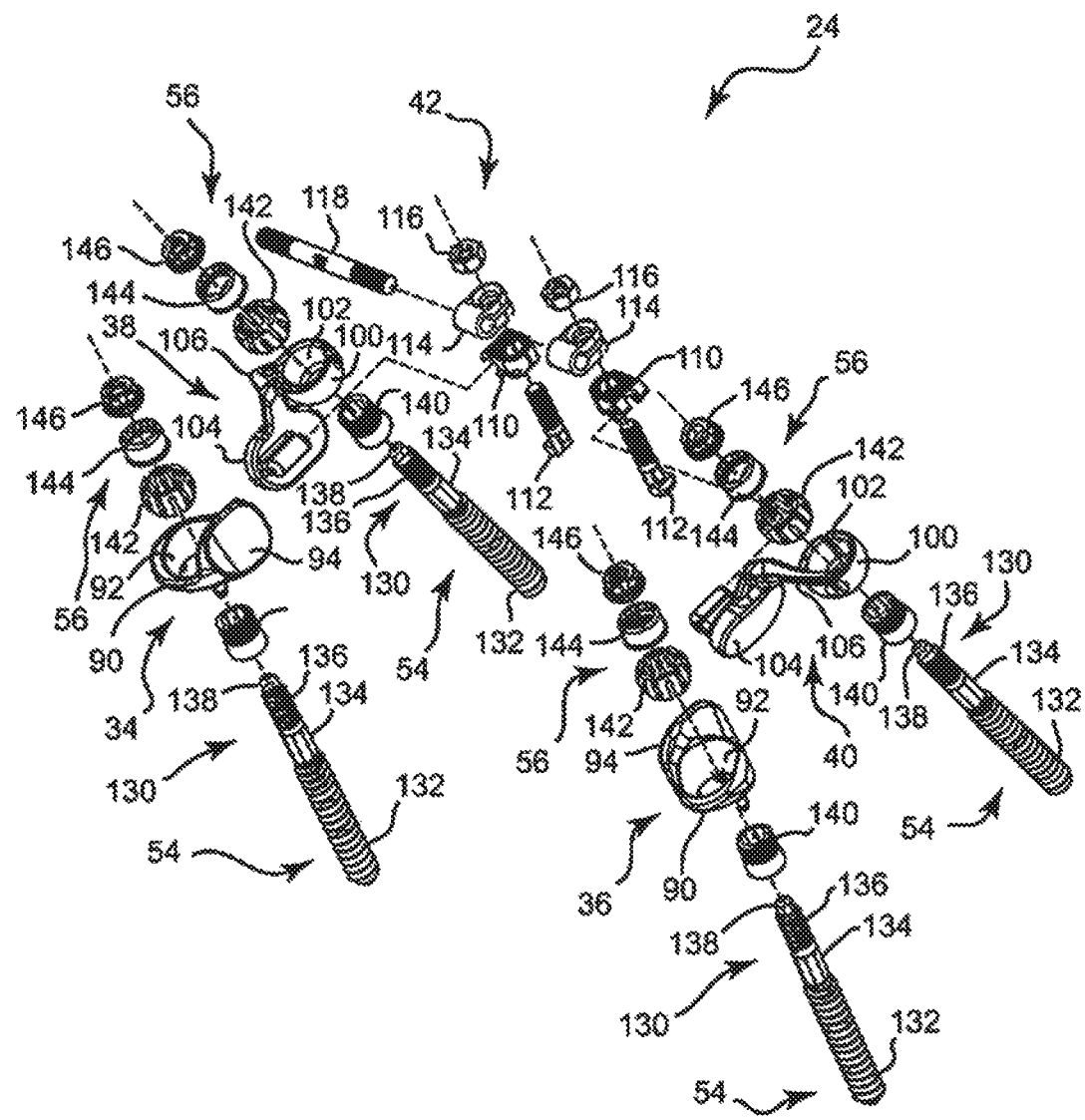
FIG. 2 is an exploded, perspective view of the caudal facet joint assembly, fixation members, and locking assemblies of the system of FIG. 1.

Referring to FIG. 2, an exploded, perspective view illustrates the caudal facet joint assembly 24, pedicle screws 54, and locking assemblies 56 of the system 10 of FIG. 1. As shown, each of the superior prostheses 34, 36 has a bone apposition surface 90, a semispherical receiving surface 92, and an articulation surface 94. Each bone apposition surface 90 is part of a mounting portion of the corresponding prosthesis 34 or 36, and may be generally conical in shape, with protruding fingers designed to engage the vertebral bone to prevent relative motion between the superior prostheses 34, 36 and the vertebra to which they are attached.

Each semispherical receiving surface 92 has a substantially concave, semispherical shape sized to receive the corresponding convex, semispherical portion of any of the superior prostheses 60, 62, the inferior prostheses 38, 40, or the inferior prostheses 48, 50. Each articulation surface 94 has a shape that is shaped to articulate with the corresponding inferior prosthesis 38 or 40. The articulation surfaces 94 may mimic the shapes of the natural superior facets, and may thus have concave, trough-like shapes or the like.

Each of the inferior prostheses 38, 40 may have a semispherical engagement surface 100, a semispherical receiving surface 102, an articulation surface 104, and a stem 106. The semispherical engagement surfaces 100 have substantially convex, semispherical shapes sized to nest within the semispherical receiving surfaces 92 of the superior prostheses 34, 36. The semispherical shapes of the semispherical receiving surfaces 92 and semispherical engagement surfaces 100 permit polyaxial adjustment of the orientation of each inferior prosthesis 38, 40 relative to the corresponding superior prosthesis 34, 36.

In this application, "polyaxial adjustability" refers to the ability to rotate the object about at least two, and possibly three, orthogonal axes relative to another object. Through the use of polyaxial adjustability, the facet joint assemblies 24, 26 are adjustable to accommodate a wide variety of spinal morphologies, and provide relatively natural articulation regardless of natural variations in vertebral geometry.

The semispherical engagement surfaces 100 may optionally be broken by slots, as shown in FIG. 2. The slots in the semispherical engagement surfaces 100 permit the semispherical engagement surfaces to contract as they are urged into the semi spherical receiving surfaces 92. The resulting expansion pressure holds the semispherical engagement and receiving surfaces 100, 92 tightly together to restrict relative motion between the superior prostheses 34, 36 and the inferior prostheses 38, 40 after the locking assemblies 56 have been tightened on the pedicle screws 54.

The semispherical receiving surfaces 102 of the inferior prostheses 38, 40 have substantially concave, semispherical shapes that are substantially concentric with the semispherical engagement surfaces 100. The semispherical receiving surfaces 102 are sized to receive corresponding convex, semispherical surfaces of the locking assemblies 56, as will be described in detail subsequently.

The articulation surfaces 104 are shaped to articulate with the articulation surfaces 94 of the superior prostheses 34, 36 in a manner that substantially duplicates the articulation of the natural facet joint replaced by the superior and inferior prostheses 34, 36, 38, 40. Thus, the articulation surfaces 104 may mimic the shapes of the natural inferior facets, and may have convex shapes. Each stem 106 connects one of the semispherical engagement surfaces 100 with the corresponding articulation surface 104 such that, upon attachment of the inferior prostheses 38, 40 to the pedicles of the corresponding vertebra, the articulation surfaces 104 are positioned at or near the locations of the removed natural inferior facets.

As also shown in FIG. 2, the crosslink assembly 42 includes two implant coupling components 110, two bolts 112, two rod coupling components 114, two nuts 116, and a rod 118. The implant coupling components 110 are shaped to be attached to the inferior prostheses 38, 40 in a manner that permits adjustment of the positioning of the implant coupling components 110 relative to the inferior prostheses 38, 40 along an axis extending generally anterior-posteriorly.

The bolts 112 can pass through holes in the implant coupling components 110 and through aligned holes in the rod coupling components 114 so that the rod coupling components 114 can be pivotably adjusted about the axes of the bolts 112 and locked in place relative to the implant coupling components 110 through the use of the nuts 116. The bolts 112 and nuts 116 are also used to secure the rod coupling components 114 to the ends of the rod 118 at the desired spacing. Thus, the crosslink assembly 42 is adjustable to suit the spacing and angulation of the inferior prostheses 38, 40, and is also easily lockable through the use of the bolts 112 and nuts 116 to provide a rigid bridge between the inferior prostheses 38, 40.

As also illustrated in FIG. 2, each of the pedicle screws 54 has a proximal end 130 that receives the corresponding locking assembly 56, and a distal end 132 with threads that facilitate implantation of the distal end 132 in the bone of the corresponding vertebra. Each proximal end 130 has a sliding interface with a substantially continuous cross section, along which the corresponding locking assembly 56 can selectively slide. In FIG. 2, the sliding interfaces are polygonal portions 134 having octagonal cross sectional shapes. Other cross sectional shapes may, of course, be used to provide a sliding interface. Each proximal end 130 also has threads 136 designed to receive the corresponding locking assembly 56, and a torquing interface 138 that can be engaged by a tool to facilitate implantation of the pedicle screw 54 in the corresponding vertebra.

Each of the locking assemblies 56 includes an interpositional member 140, an engagement member 142, a rotational locking member 144, and a translational locking member 146. Each interpositional member 140 has exterior threads, a flared end, and a bore shaped to slide along the polygonal portion 134 of the corresponding pedicle screw 54. Each engagement member 142 may take the form of a split sphere 142 with a plurality of slots that permit expansion and contraction of the split sphere 142. Each split sphere 142 has a hollow interior in which the corresponding interpositional member 140 may be positioned, such that the flared end of the interpositional member protrudes from the distal end of the split sphere 142.

Each of the rotational locking members 144 includes interior threads that engage the exterior threads of the corresponding interpositional member 140. Thus, the split sphere 142 may be compressed between the rotational locking member 144 and the flared end of the attached interpositional member 140. In response to the compression, the flared end urges outward expansion of the split sphere 142 so that the outer surface of the split sphere 142 engages the semispherical receiving surface 102 of the corresponding inferior prosthesis 38 or 40. Due to the slotted geometry of the semispherical engagement surface 100, the resulting radial pressure on the semispherical receiving surface 102 causes expansion of the corresponding semispherical engagement surface 100. Thus, the semispherical engagement surface 100 expands to press against the semispherical receiving surface 92 of the corresponding superior prosthesis 34 or 36.

Accordingly, threaded tightening of a rotational locking member 144 relative to an interpositional member 140, with the interpositional member 140 positioned on the polygonal portion 134 of a pedicle screw 54, restricts relative rotation between the pedicle screw 54, the locking assembly 56, the inferior prosthesis 38 or 40, and the superior prosthesis 34 or 36. Advantageously, the locking assembly 56 is still slidable along the pedicle screw 54 until the associated translational locking member 146 is tightened on the threads 136 of the proximal end 130 of the pedicle screw 54. Once the translational locking member 146 is tightened, it presses the remainder of the locking assembly 56, the inferior prosthesis 38 or 40, and the superior prosthesis 34 or 36 against the bony apposition surface of the corresponding vertebra to prevent further sliding of the locking assembly 56, the inferior prosthesis 38 or 40, and the superior prosthesis 34, 36 relative to the pedicle screw 54.

Figure 3:
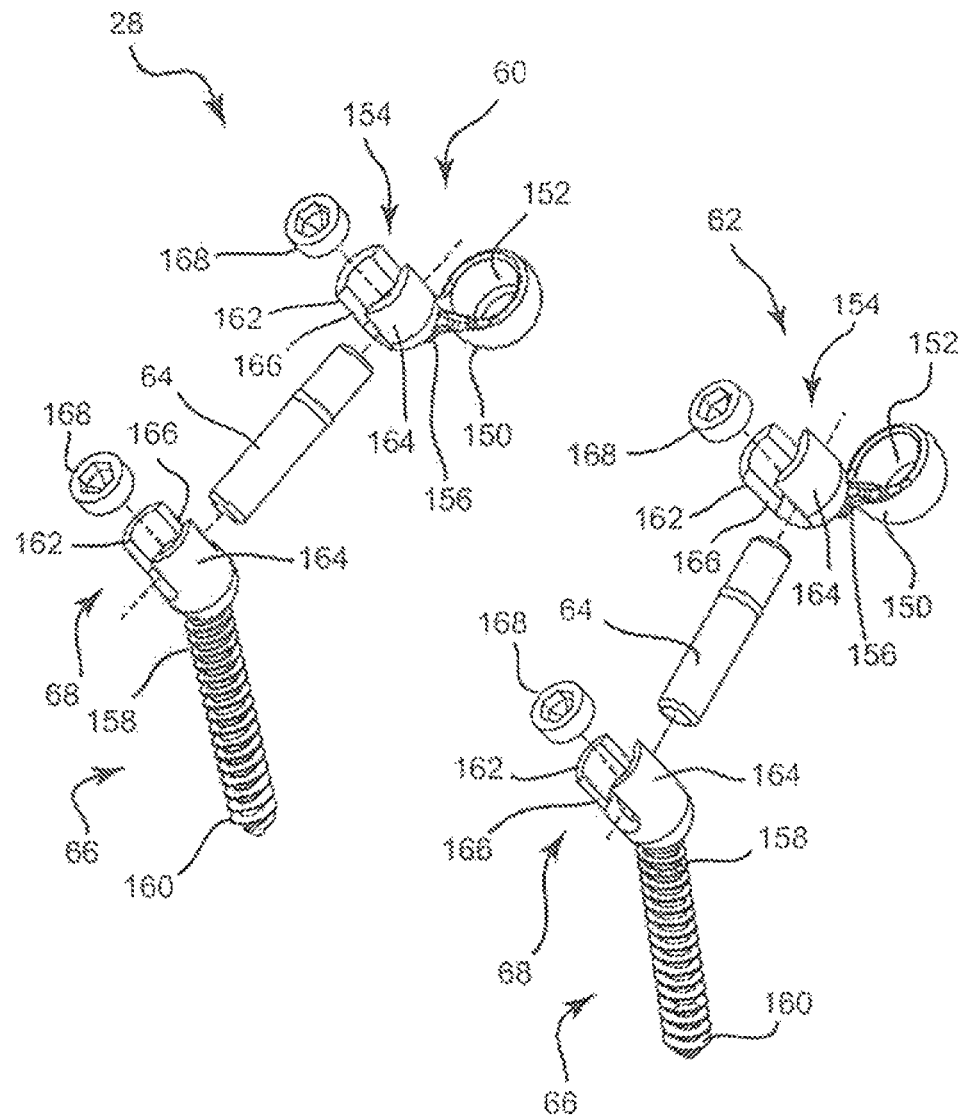
FIG. 3 is an exploded, perspective view of the caudal fusion assembly, fixation members, and yoke assemblies of the system of FIG. 1.

Referring to FIG. 3, an exploded, perspective view illustrates the caudal fusion assembly 28, pedicle screws 66, and yoke assemblies 68 of the system 10 of FIG. 1. As shown, each of the inferior prostheses 60, 62 has a semispherical engagement surface 150, a semispherical receiving surface 152, a yoke assembly 154, and a stem 156. Each semispherical engagement surface 150 has a convex, substantially semispherical shape sized to nest within the semispherical receiving surface 92 of the corresponding superior prosthesis 34 or 36. Each semispherical engagement surface 150 may optionally have a slotted configuration like that of the semispherical engagement surfaces 100 of the inferior prostheses 38, 40 shown in FIG. 2. However, as embodied in FIG. 3, the semispherical engagement surfaces 150 are not slotted.

Each of the semispherical receiving surfaces 152 has a concave, substantially semispherical shape sized to receive the outer surfaces of the split spheres 142 of the locking assemblies 56 in a manner similar to that of the semispherical receiving surfaces 102 of the inferior prostheses 38, 40. Each yoke assembly 154 is shaped to receive the cephalad end of one of the rods 64. The yoke assemblies 154 are connected to the semispherical engagement surfaces 150 by the stems 156.

The pedicle screws 66 are configured differently from the pedicle screws 54 because the pedicle screws 66 are designed to receive the yoke assemblies 68 instead of the locking assemblies 56. Thus, each of the pedicle screws 66 has a proximal end 158 and a distal end 160. The proximal end 158 may have a head (not visible) with a semispherical undercut that permits polyaxial rotation of the corresponding yoke assembly 68 relative to it, until the yoke assembly 68 is locked. Each distal end 160 may be threaded to permit implantation in the pedicle of a vertebra.

Each of the yoke assemblies 68, 154 may have a configuration similar to that of known polyaxial yokes, or may be configured differently from known systems. As embodied in FIG. 3, each yoke assembly 68, 154 has a first wall 162 and a second wall 164 that extend generally parallel to each other to define a trough 166 that extends between the first and second walls 162, 164. Each of the first and second walls 162, 164 has threads (not shown) on the interior, concave surface. Each yoke assembly 68, 154 may also have a nut 168 with exterior threads (not shown) that can be threadably engaged with the threads of the corresponding walls 162, 164 to advance the nut 168 toward the trough 166.

When the ends of the rods 64 are positioned in the troughs 166 of the yoke assemblies 68, 154, tightening the nuts 168 causes the nuts 168 to press the ends of the rods 64 into the troughs 166 such that the ends of the rods 64 are captured by the yoke assemblies 68, 154. In the case of the yoke assemblies 68, tightening the nuts 168 against the ends of the rods 64 may also cause the rods 64 to press against the proximal ends of the pedicle screws 66, thereby restricting or preventing relative rotation between the yoke assemblies 68 and the pedicle screws 66. Advantageously, the polyaxial adjustability of the yoke assemblies 68 prior to tightening of the nuts 168 permits attachment of the caudal ends of the rods 64 to the pedicle screws 66 at a wide variety of relative orientations, thereby permitting the caudal fusion assembly with a wide variety of spinal morphologies.

Figure 4:
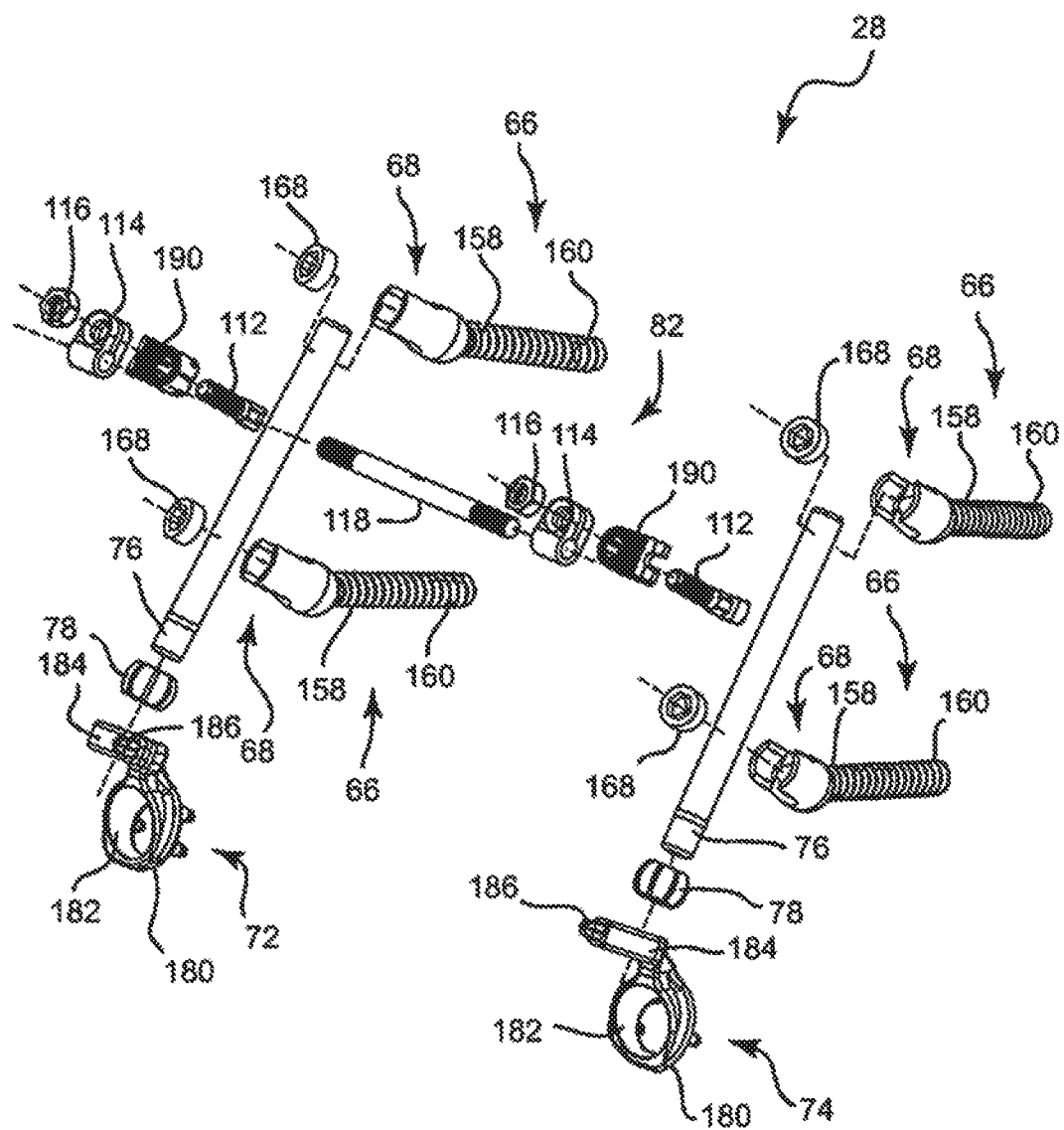
FIG. 4 is an exploded, perspective view of the cephalad fusion assembly, fixation members, and yoke assemblies of the system of FIG. 1.

Referring to FIG. 4, an exploded, perspective view illustrates the cephalad fusion assembly 30, pedicle screws 66, and yoke assemblies 68 of the system of FIG. 1. As shown, each of the inferior prostheses 72, 74 of the cephalad fusion assembly 30 has a bone apposition surface 180, a semispherical receiving surface 182, a polyaxial receiver 184, and a receiver fastener 186.

The bone apposition surfaces 180 are substantially the same as the bone apposition surfaces 90 of the superior prostheses 34, 36 of the caudal facet joint assembly 24. Thus, each of the bone apposition surfaces 180 may be generally conical in shape, with protruding fingers designed to engage the vertebral bone to prevent relative motion between the inferior prostheses 72, 74 and the vertebra to which they are attached.

The semispherical receiving surfaces 182 may be substantially the same as the semispherical receiving surfaces 92 of the superior prostheses 34, 36 of the caudal facet joint assembly. Thus, each of the semispherical receiving surfaces 182 may have a substantially concave, semispherical shape sized to receive the corresponding convex, semispherical portion of any of the superior prostheses 60, 62, the inferior prostheses 38, 40, or the inferior prostheses 48, 50.

Each of the rod connectors 78 may have a substantially semispherical shape with slots that permit expansion or contraction of the rod connectors 78. The rod connectors 78 may have bores (not visible) sized to receive the caudal ends of the rods 76. The exterior surfaces of the rod connectors 78 may be compressed to substantially radially compress the caudal ends of the rods 76, thereby providing a tight attachment between the rod connectors 78 and the caudal ends of the rods 76.

Each of the polyaxial receivers 184 extends form the corresponding bone apposition surface 180 and has a concave, semispherical bore (not visible) shaped to receive the corresponding polyaxial rod connector 78 in a manner that permits polyaxial rotation between the rod connector 78 and the polyaxial receiver 184. Thus, each polyaxial receiver 184 can receive the caudal end of the corresponding rod 76 at any of a plurality of relative orientations. This permits usage of the cephalad fusion assembly 30 with a wide variety of spinal morphologies.

The receiver fasteners 186 are used to tighten the concave, semispherical bores of the polyaxial receivers 184 around the rod connectors 78. The receiver fasteners 186 may take the form of small screws that can be tightened to cause contraction of the concave, semispherical bores of the polyaxial receivers 184 around the rod connectors 78. In response to contraction of the concave, semispherical bores, the rod connectors 78 tighten around the caudal ends of the rods 76 so that the rods 76 become rigidly secured to the inferior prostheses 72, 74.

The pedicle screws 66 and yoke assemblies 68 are identical to those described in connection with FIG. 3. Accordingly, the yoke assemblies 68 are polyaxially rotatable relative to the pedicle screws 66 to permit them to receive the cephalad ends of the rods 76 at any of a plurality of relative orientations. Like those of FIG. 3, the orientations of the yoke assemblies 68 may also be locked relative to the pedicle screws 66 by tightening the nuts 168 against the cephalad ends of the rods 76.

As embodied in FIG. 4, the crosslink assembly 82 is very similar to the crosslink assemblies 42, 52 of the facet joint assemblies 24, 26. Accordingly, the crosslink assembly 82 has two rod coupling components 190, two bolts 112, two rod coupling components 114, two nuts 116, and a rod 118. The rod coupling components 190 may be very similar to the implant coupling components 110 of the crosslink assemblies 42, 52, except that the rod coupling components 190 are sized to grip the rods 76 of the caudal fusion assembly 28 instead of the inferior prostheses 38, 40. The bolts 112, 114, nuts 116, and rod 118 function in a manner very similar to that described in connection with FIG. 2, in the description of the crosslink assembly 42 of the caudal facet joint assembly 24. Thus, the crosslink 82 may be adjusted to accommodate different positions of the rods 76, and may then be tightened to provide a rigid bridge between the rods 76.

The system 10 of FIG. 1 effectively replaces the natural facets of two spinal motion segments with prosthetic facets, fuses the motion segment immediately inferior to the prosthetic facets, and also fuses the two motion segments immediately superior to the prosthetic facets. The system 10 is modular in design, and can therefore be used for any combination of facet joint replacement and fusion, whether one or multiple motion segments are to receive facet joint replacement or fusion, and whether or not the motion segments to be treated are adjacent to each other.

Figure 5:
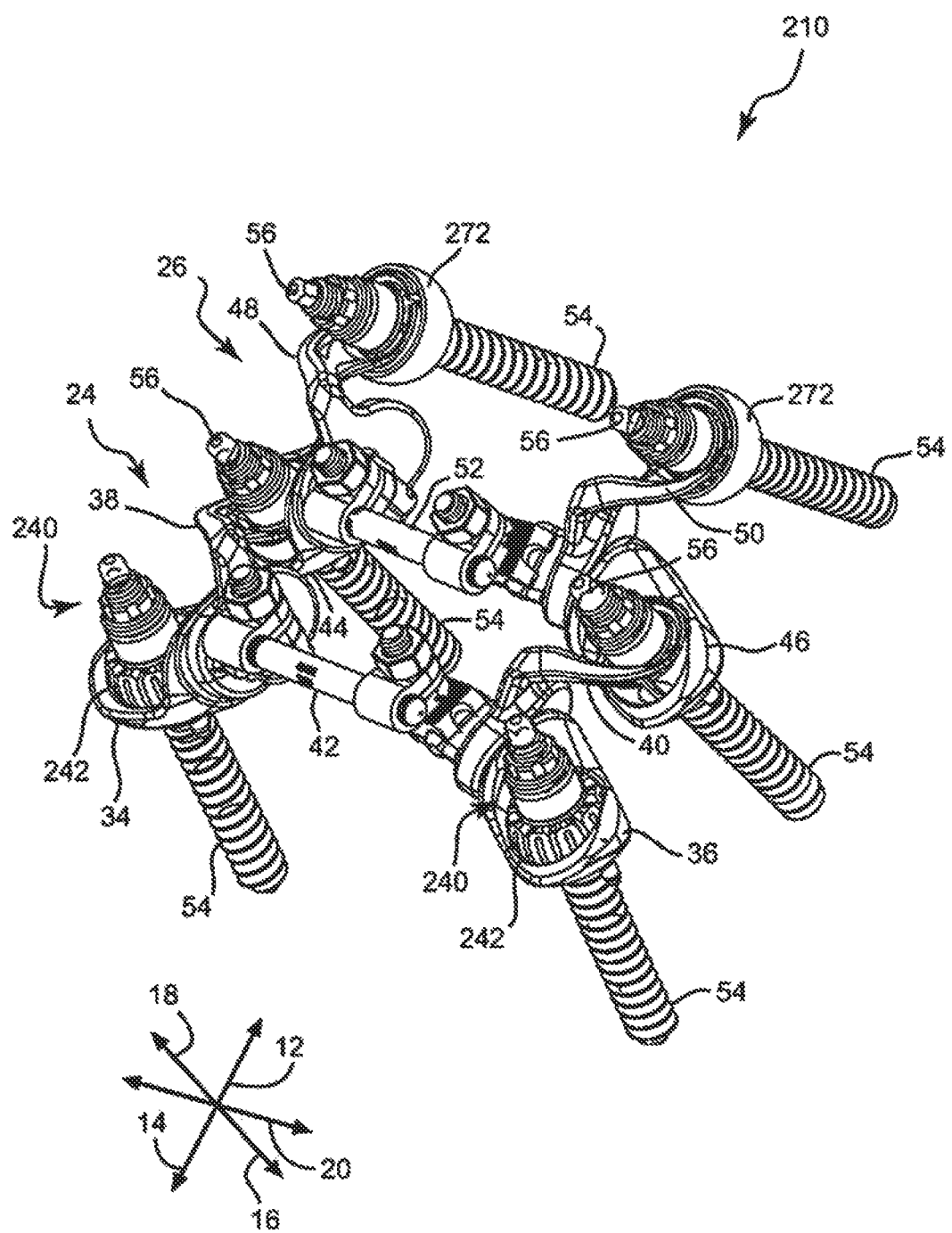
FIG. 5 is a perspective view of a system according to one alternative embodiment of the invention, in which multiple level facet joint replacement may be carried out without adjacent level fusion.

Referring to FIG. 5, a perspective view illustrates a system 210 according to one alternative embodiment of the invention, in which multiple level facet joint replacement may be carried out without adjacent level fusion. As shown, the system 210 includes the caudal facet joint assembly 24 and the cephalad facet joint assembly 26 of FIG. 1. However, the caudal fusion assembly 28 and the cephalad fusion assembly 30 have been omitted.

In place of the caudal locking assemblies 56 of the caudal facet joint assembly 24, locking assemblies 240 are provided. Since the caudal fusion assembly 28 is not present, the superior prostheses 60, 62 of the caudal fusion assembly 28 are not nested within the semispherical receiving surfaces 92 of the superior implants 34, 36 of the caudal facet joint assembly 24. To fill the space that would otherwise be taken by the superior prostheses 60, 62, the locking assemblies 240 include engagement members 242 that take the place of the split spheres 142 included in the locking assemblies 56. The engagement members 242 are larger than the split spheres 142 and will be shown and described in connection with FIG. 6.

The inferior prostheses 72, 74 of the cephalad fusion assembly 30 also are not present. To fill the space that would otherwise be taken the by inferior prostheses 72, 74, in-growth cups 272 may be provided. The in-growth cups receive the semispherical engagement surfaces 100 of the inferior prostheses 48, 50 of the cephalad fusion assembly 26 in a manner similar to that of the inferior prostheses 72, 74, as will be described in connection with FIG. 7.

Advantageously, the remaining components of the system 210 are substantially the same as those of the system 10. Accordingly, a kit can easily be provided, including the facet joint assemblies 24, 26, fusion assemblies 28, 30, pedicle screws 54, 66, locking assemblies 56, yoke assemblies 68, engagement members 242, and in-growth cups 272. Such a kit would enable the surgeon to select the components needed for either of the systems 10, 210, thereby providing maximum flexibility and minimizing inventory.

Figure 6:
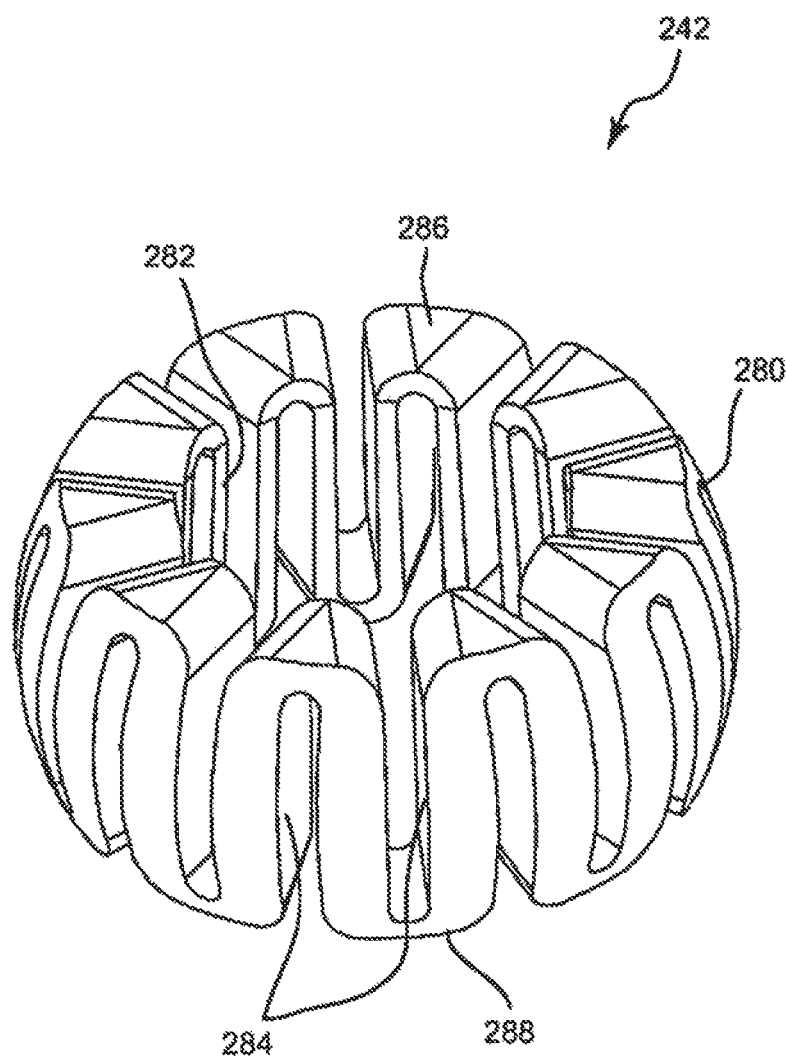
FIG. 6 is a perspective view of one of the engagement members of the system of FIG. 5.

Referring to FIG. 6, a perspective view illustrates one of the engagement members 242 of the system 210 of FIG. 5.

As shown, the engagement member 242 has an interior surface 282 with a generally cylindrical shape broken by slots 284. The engagement member 242 also has a proximal shoulder 286 and a distal shoulder 288. Like those of the split spheres 142, the proximal shoulder 286 of the engagement member 242 may receive pressure from the associated rotational locking member 144 to urge the distal shoulder 288 to slide over the flared portion of the corresponding interpositional member 140, thereby causing expansion of the distal portion of the engagement member 242.

The outer surface of the engagement member 242 then presses directly against the semispherical receiving surface 92 of the corresponding superior prosthesis 34 or 36 of the caudal facet joint assembly 24. The larger size of the engagement members 242 relative to the split spheres 142 enables the locking assemblies 240 to operate in a manner similar to that of the locking assemblies 56, without requiring the presence of the superior prostheses 60, 62 of the caudal fusion assembly 28.

Figure 7:
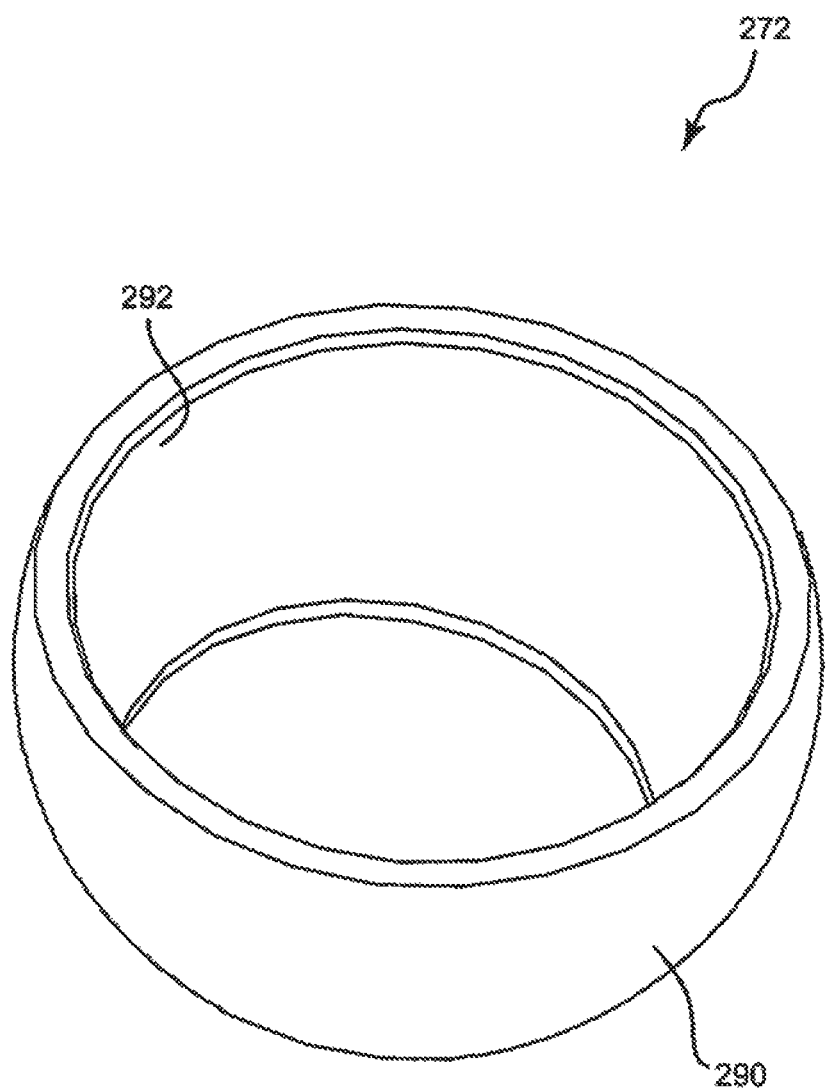
FIG. 7 is a perspective view of one of the in-growth cups of the system of FIG. 5.

Referring to FIG. 7 a perspective view illustrates one of the in-growth cups 272 of the system 210 of FIG. 5. As shown, the in-growth cup 272 has a bone apposition surface 290 and a semispherical receiving surface 292. The bone apposition surface 290 may be semispherical as illustrated in FIG. 7, or may be shaped differently. For example, in alternative embodiments, an in-growth cup (not shown) may have a bone apposition surface with a generally conical shape, with or without the fingers utilized by the bone apposition surfaces 90 of the superior prostheses 34, 36, 44, 46. The bone apposition surface 290 may also be porous and/or textured to facilitate bone in-growth into the in-growth cup 272.

The semispherical receiving surface 292 may be shaped substantially the same as the semispherical receiving surfaces 92 of the superior prostheses 34, 36, 44, 46. Accordingly, the semispherical receiving surface 292 may be sized to receive the corresponding convex, semispherical portion of any of the superior prostheses 60, 62, the inferior prostheses 38, 40, or the inferior prostheses 48, 50. Thus, the in-growth cups 272 fill the spaces left by the omission of the inferior prostheses 72, 74 of the cephalad fusion assembly 30.

Facet joint replacement and/or fusion systems according to the invention may be implanted through the use of a wide variety of procedures. FIGS. 8 through 17 illustrate one procedure by which a system similar to the system 10 of FIG. 1 may be implanted. The system to be shown in FIGS. 8 through 17 provides facet joint replacement for two adjacent spinal motion segments, and fusion for the motion segments immediately inferior and superior to them.

Figure 8:
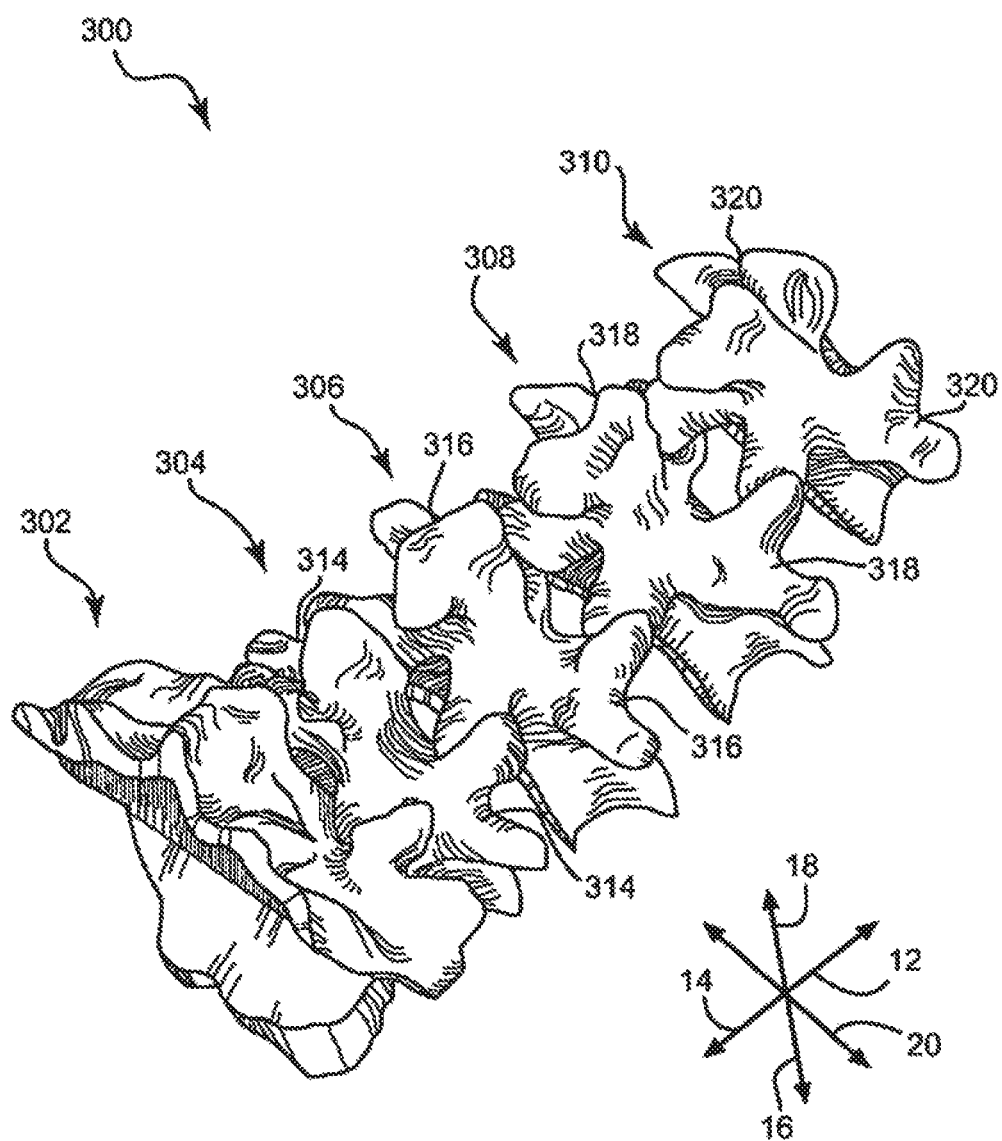
FIG. 8 is a perspective view of a portion of a spine to which the system of FIG. 1 or the system of FIG. 5 may be secured to provide multiple level facet joint replacement with or without adjacent level fusion.

Referring to FIG. 8, a perspective view illustrates a portion of a spine 300 to which the system 10 of FIG. 1 or the system 210 of FIG. 5 may be secured to provide multiple level facet joint replacement with or without adjacent level fusion. As shown, the spine 300 includes a first vertebra 302, a second vertebra 304, a third vertebra 306, a fourth vertebra 308, and a fifth vertebra 310. The vertebrae 302, 304, 306, 308, 310 may represent S1, L5, L4, L3, and L2, respectively. Alternatively, the vertebrae 302, 304, 306, 308, 310 may represent other vertebrae of the spine 300.

As illustrated in FIG. 8, the vertebrae 302, 304, 306, 308, 310 have many anatomical structures known to those of skill in the art. These anatomical structures include pedicles 314 of the second vertebra 304, pedicles 316 of the third vertebra 306, pedicles 318 of the fourth vertebra 308, and pedicles 320 of the fifth vertebra 310.

The articular processes of the vertebrae 304, 306, 308, 310 may first be resected. The articular processes providing the joints between the second and third vertebrae 304, 306 and between the third and fourth vertebrae 306, 308 are resected to enable their prosthetic counterparts to be positioned in such a manner that substantially natural articulation is provided. The articular processes providing the joints between the first and second vertebrae 302, 304 and between the fourth and fifth vertebrae 308, 310 may be left intact because they may not interfere with implantation of the fusion components. Alternatively, the articular processes providing the joints between the first and second vertebrae 302, 304 and/or between the fourth and fifth vertebrae 308, 310 may be resected to facilitate implantation of the fusion components and/or to remove diseased or brittle bone.

Figure 9:
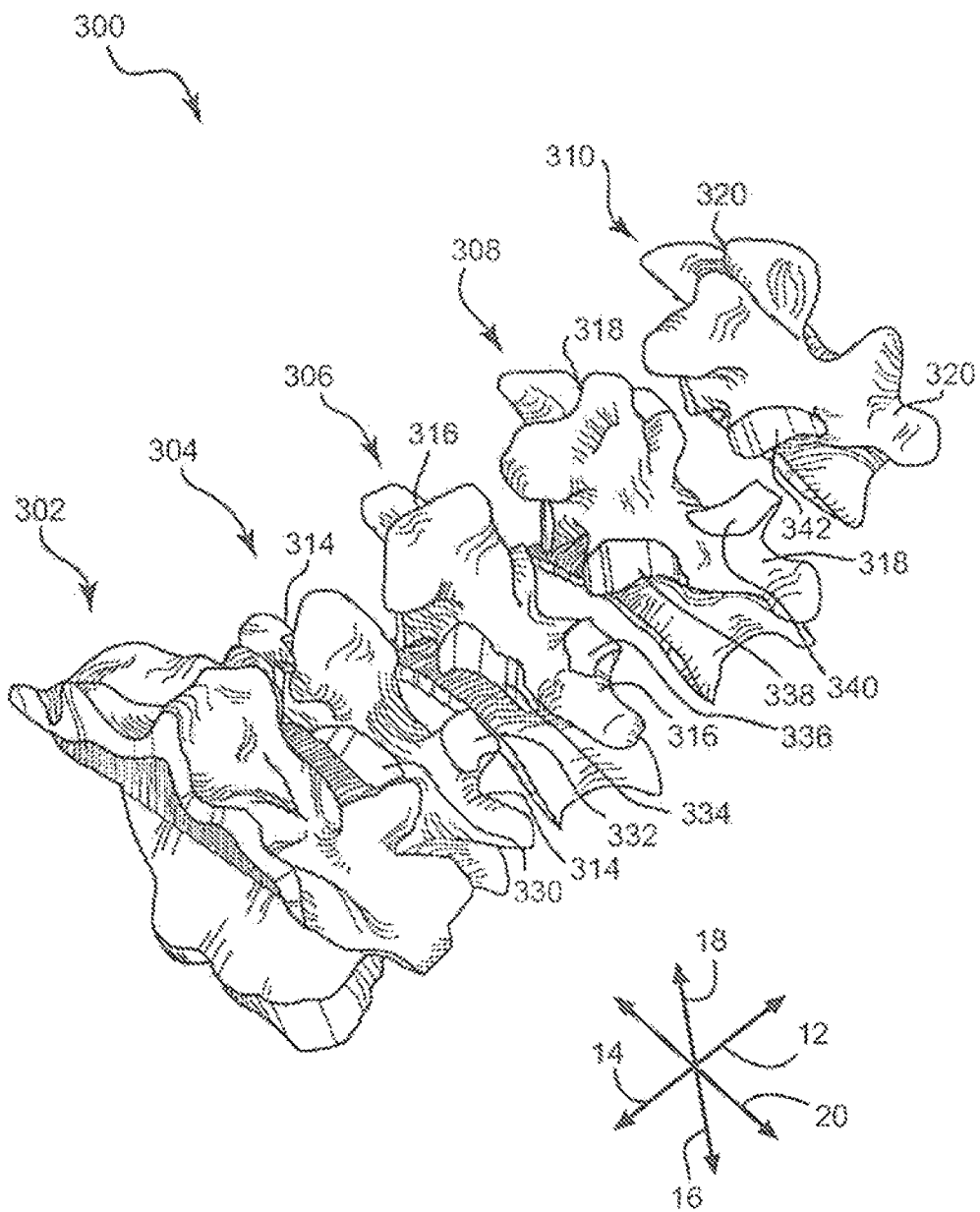
FIG. 9 is a perspective view of the portion of the spine of FIG. 8 after resection of some of the natural articular surfaces of the vertebrae.

Referring to FIG. 9, a perspective view illustrates the portion of the spine 300 of FIG. 8 after resection of some of the natural articular surfaces of the vertebrae 304, 306, 308, 310. More precisely, the superior and inferior articular processes of the second vertebra 304 have been resected away, leaving two inferior resections 330 and two superior resections 332. The superior and inferior articular processes of the third vertebra 306 have been resected away, leaving two inferior resections 334 and two superior resections 336. The superior and inferior articular processes of the fourth vertebra 308 have been resected away, leaving two inferior resections 338 and two superior resections 340. The inferior articular processes of the fifth vertebra 310 have been resected away, leaving two inferior resections 342.

According to one exemplary method, the resections 330, 332, 334, 336, 338, 340, 342 need not be made at any precise angle or location. After the articular processes have been resected away, guide wires may be implanted in the vertebrae 304, 306, 308, 310. The guide wires may be used to guide further steps.

Figure 10:
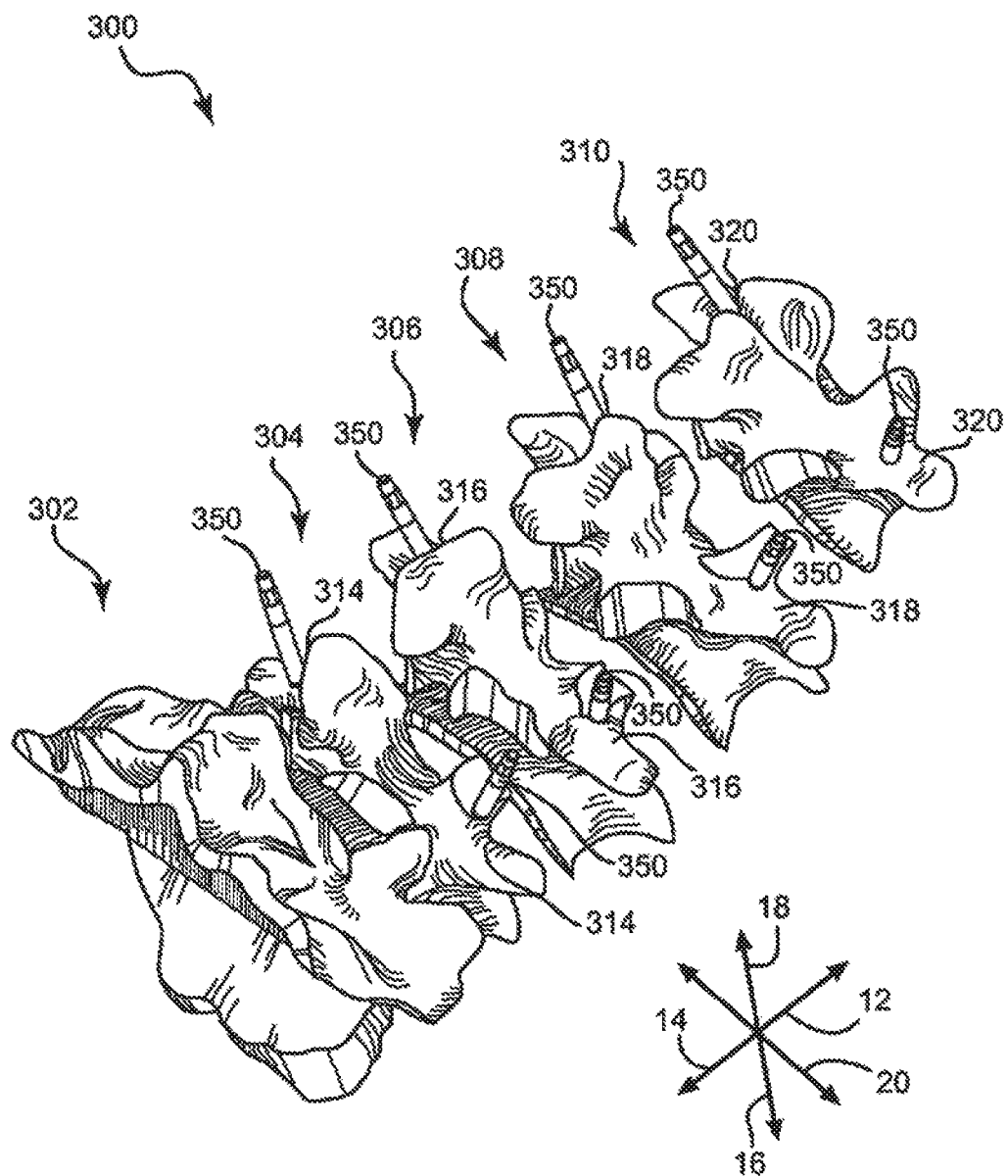
FIG. 10 is a perspective view of the portion of the spine of FIG. 8 after implantation of guide wires in the pedicles of some of the vertebrae.

Referring to FIG. 10, a perspective view illustrates the portion of the spine 300 of FIG. 8 after implantation of guide wires 350 in the pedicles 314, 316, 318, 320 of the second, third, fourth, and fifth vertebrae 304, 306, 308, 310. The guide wires 350 may be configured and implanted in a variety of ways, many of which are known in the art. Each guide wire 350 is implanted along the axis of one of the pedicles 314, 316, 318, 320. If the first vertebra 302 is S1, guide wires 350 may not be needed in the first vertebra 302 to locate sufficient bone mass for anchoring the caudal fusion assembly 28 to the first vertebra 302. After the guide wires 350 have been implanted, the saddle points of the pedicles 314, 316, 318, 320 of the second, third, fourth, and fifth vertebrae 304, 306, 308, 310 may be reamed to provide semispherical resections.

Figure 11:
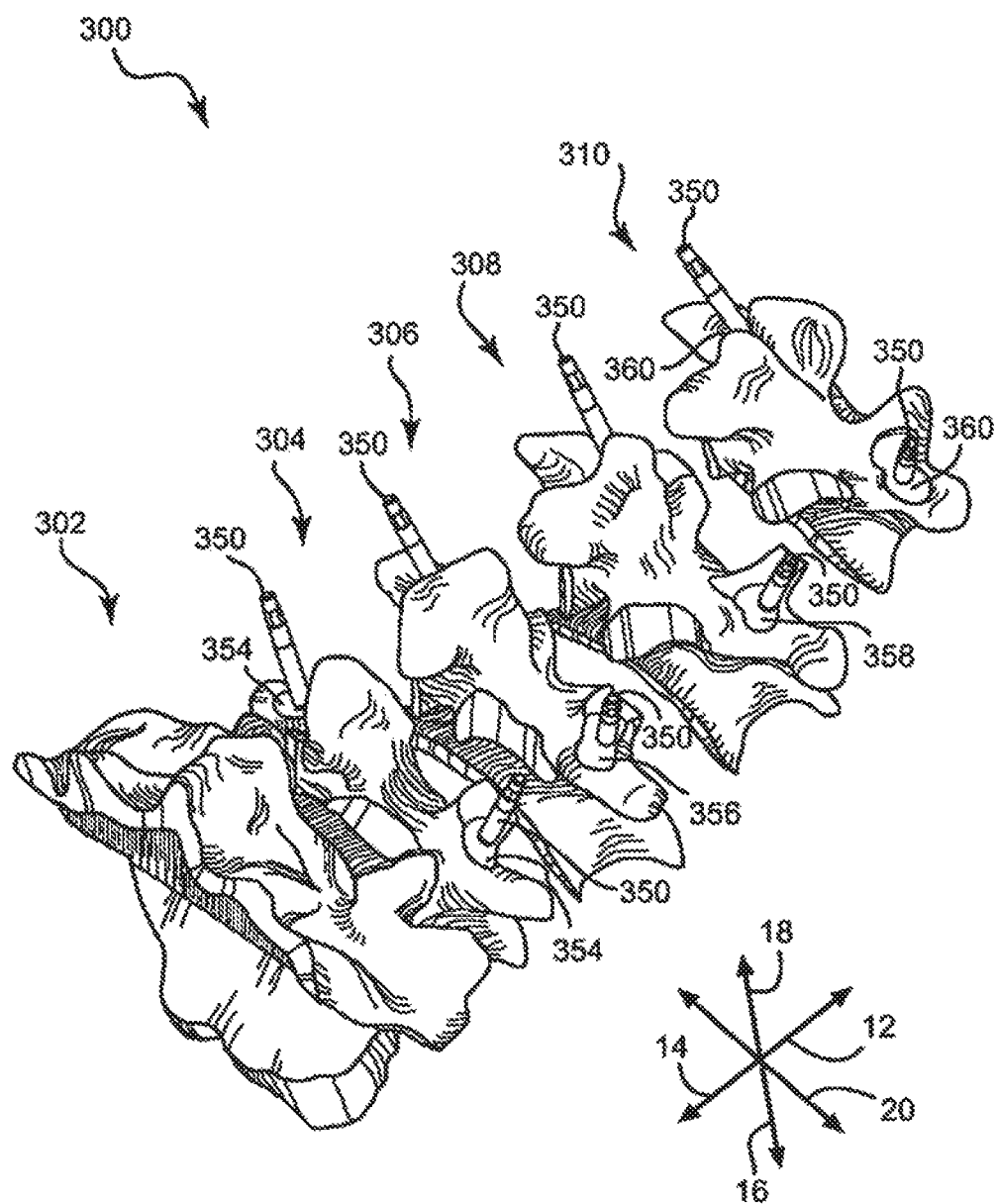
FIG. 11 is a perspective view of the portion of the spine of FIG. 8 after reaming of the pedicle saddle points to provide semispherical resections.

Referring to FIG. 11, a perspective view illustrates the portion of the spine 300 of FIG. 8 after reaming of the saddle points of the pedicles 314, 316, 318, 320 to provide semispherical resections 354, 356, 358, 360. More precisely, after the reaming operation has been carried out, the second vertebra 304 has semispherical resections 354, the third vertebra 306 has semispherical resections 356, the fourth vertebra 308 has semispherical resections 358, and the fifth vertebra 310 has semispherical resections 360. The semispherical resections 354 on the second vertebra 304 are optional, and may be omitted if desired.

Figure 12:
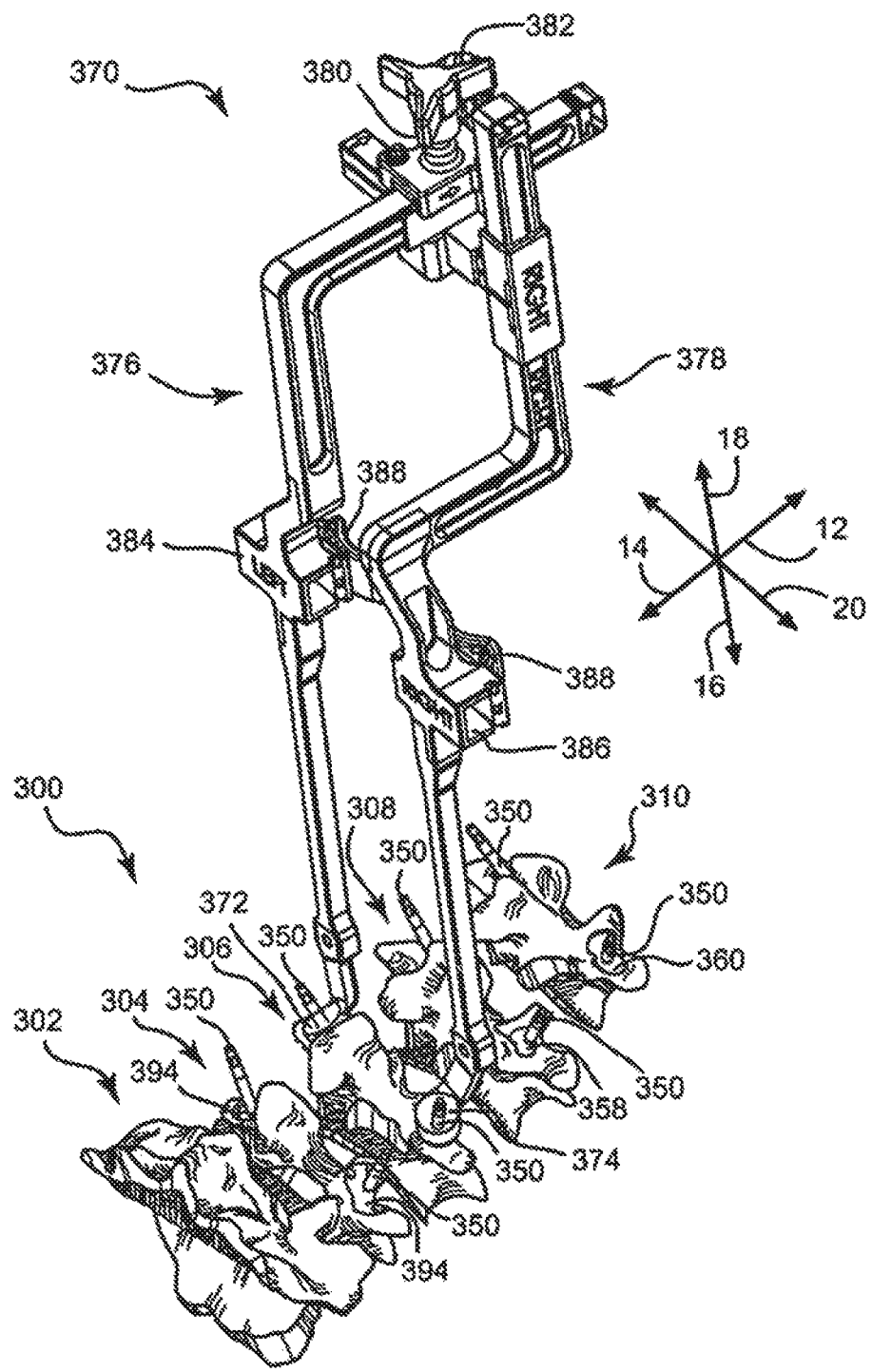
FIG. 12 is a perspective view of the portion of the spine of FIG. 8 with a frame registered on the third vertebra to facilitate formation of shaped resections on the saddle points of the second vertebra.

Reaming may be accomplished through the use of a reamer (not shown) with a rotating, semispherical head having a longitudinal bore designed to receive the protruding proximal ends of each of the guide wires 350. Thus, the guide wires 350 guide the reaming operations to ensure that the semispherical resections 354, 356, 358, 360 have the proper shape and size. After reaming of the saddle points of the pedicles 314, 316, 318, 320 has been carried out, the saddle points of the pedicles 314 of the second vertebra 304 may be further reamed and prepared to receive the superior prostheses 34, 36 of the caudal facet joint assembly 24. Referring to FIG. 12, a perspective view illustrates the portion of the spine 300 of FIG. 8 with a frame 370 registered on the third vertebra 306 to facilitate formation of shaped resections on the saddle points of the pedicles 314 second vertebra 304. As shown, the frame 370 has a first anchor 372, a second anchor 374, a first arm 376, a second arm 378, a locking mechanism 380, and an external anchoring feature 382.

The anchors 372, 374 have semispherical distal ends designed to fit into the semispherical resections 356 of the third vertebra 306 in such a manner that the frame 370 can be oriented within the sagittal plane (not shown) to position it substantially perpendicular to the spine 300. The first anchor 372 attached to the distal end of the first arm 376, and the second anchor 374 is attached to the distal end of the second arm 378.

The frame 370 permits relative translation between the first and second arms 376, 378 along three perpendicular axes. Relative motion of the arms 376, 368 along all three axes may be locked through the use of a locking mechanism 380. The external anchoring feature 382 may be used to secure the frame 370 to a stationary object such as an operating table. An articulating, lockable arm (not shown) or the like may be used to grip the substantially semispherical external anchoring feature 382 to keep the frame 370 at its desired position and orientation.

In operation, the surgeon may position the anchors 372, 374 at the semispherical resections 356 and then rotate the frame 370 to the desired orientation while moving the arms 376, 378 as needed relative to each other to keep the anchors 372, 374 on the semispherical resections 356. Once the frame 370 is in the proper orientation (i.e., generally perpendicular to the spine 300 and within the sagittal plane), the surgeon may actuate the locking mechanism 380 to lock the positions of the arms 376, 378 relative to each other and secure the external anchoring feature to the stationary object to keep the frame 370 in the desired orientation.

As shown in FIG. 12, the first arm 376 has a first registration feature designed to receive one or more tools such as resection tools. As embodied in FIG. 12, the first registration feature takes the form of a first receiver 384 with a substantially rectangular bore. Similarly, the second arm 378 has a second receiver 386 with a substantially rectangular bore. The substantially rectangular bores of the receivers 384, 386 are designed to receive corresponding protruding anchoring features of the tools, and to retain the anchoring features in response to actuation of clips 388 on the receivers 384, 386. The clips 388 may compress the substantially rectangular bores to cause the receivers 384, 386 to securely retain the protruding anchoring features of the tools.

A reamer with hollow reaming head (not shown) may be secured to each of the receivers 384, 386 and used to further ream the saddle points of the pedicles 314 of the second vertebra 304. The hollow reaming head may engage the protruding proximal ends of the guide wires 350 attached to the second vertebra 304, and may have a generally conical reaming surface that forms shaped resections 394 in the second vertebra 304, as shown.

The shaped resections 394 may also have smaller holes for receiving the fingers of the bone apposition surfaces 90 of the superior prostheses 34, 36 of the caudal facet joint assembly 24. The smaller holes may be formed through the use of a smaller reamer (not shown) applied through the openings of a template (not shown), or the like. After the shaped resections 394 have been formed on the second vertebra 304, the caudal fusion assembly 28 and the superior prostheses 34, 36 of the caudal facet joint assembly 24 may be secured to the first and second vertebrae 302, 304.

Figure 13:
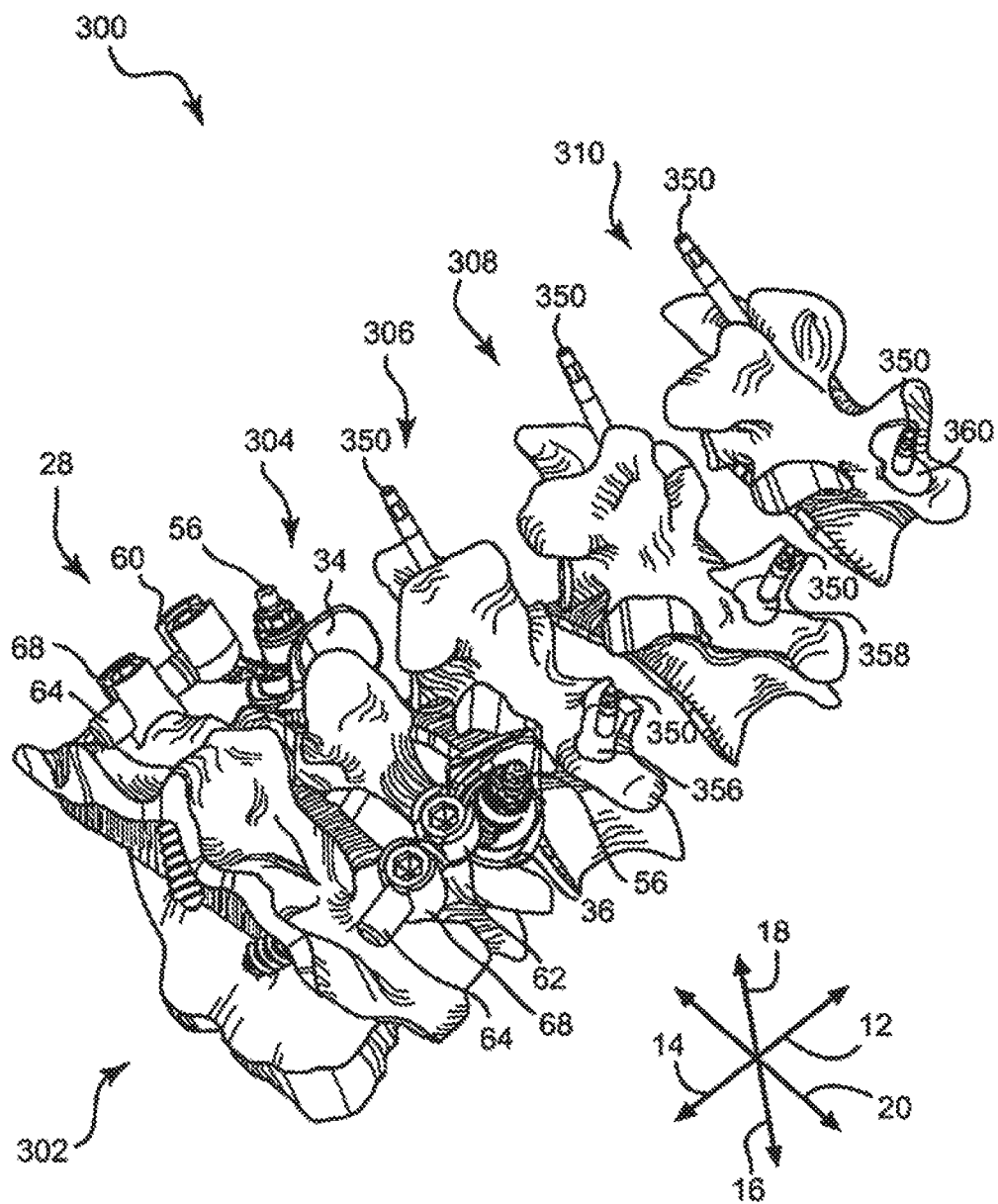
FIG. 13 is a perspective view of the portion of the spine of FIG. 8 after attachment of the caudal fusion assembly and the superior prostheses of the caudal facet joint assembly of the system of FIG. 1 to the portion of the spine.

Referring to FIG. 13, a perspective view illustrates the portion of the spine 300 of FIG. 8 after attachment of the caudal fusion assembly 28 and the superior prostheses 34, 36 of the caudal facet joint assembly 24 of the system of FIG. 1 to the first and second vertebrae 302, 304. More precisely, the guide wires 350 are removed and the pedicle screws 54 are implanted in the pedicles 314 of the second vertebra 304, along the bores that remain after removal of the guide wires 350. The superior prostheses 34, 36 are positioned on the second vertebra 304 such that the fingers of the bone apposition surfaces 90 engage the small holes of the shaped resections 394.

The pedicle screws 66 are implanted in the first vertebra 302. If the first vertebra 302 is S1, implantation of the pedicle screws 66 is not in a pedicle, but is carried out in a portion of the sacrum with sufficient bone mass to provide anchorage. This may be accomplished through the use of any of a number of methods known in the art. The pedicle screws 66 are implanted with the yoke assemblies 68 in place on the proximal ends 158 of the pedicle screws 66.

The superior prostheses 60, 62 of the caudal fusion assembly 28 are then positioned such that the semispherical engagement surfaces 150 of the superior prostheses 60, 62 rest within the semispherical receiving surfaces 92 of the superior prostheses 34, 36. The yoke assemblies 68, 154 are then polyaxially rotatable relative to the first and second vertebrae 302, 304, respectively. The yoke assemblies 68, 154 are rotated to the optimal orientations for receiving the rods 64, and the rods 64 are positioned in the troughs 166 of the yoke assemblies 68, 154. The nuts 168 are threaded into engagement with their associated arms 162, 164 and tightened to keep the rod 64 in place and restrain further pivoting of the yoke assemblies 68, 154.

Then, the interpositional members 140, the split spheres 142, and the rotational locking members 144 are inserted on the distal ends 132 of each of the pedicle screws 54 and tightened to restrict rotation of the superior prostheses 60, 62 relative to the pedicle screws 54. The translational locking members 146 are then inserted on the distal ends 132 of the pedicle screws 54 and tightened to restrict sliding of the superior prostheses 34, 36, 60, 62 away from the second vertebra 304.

This provides the configuration shown in FIG. 13, in which the caudal fusion assembly 28 and the superior prostheses 34, 36 of the caudal facet joint assembly 24 are secured to the first and second vertebrae 302, 304. Next, the pedicles 316 of the third vertebra 306 may be further reamed like those of the second vertebra 304.

Figure 14:
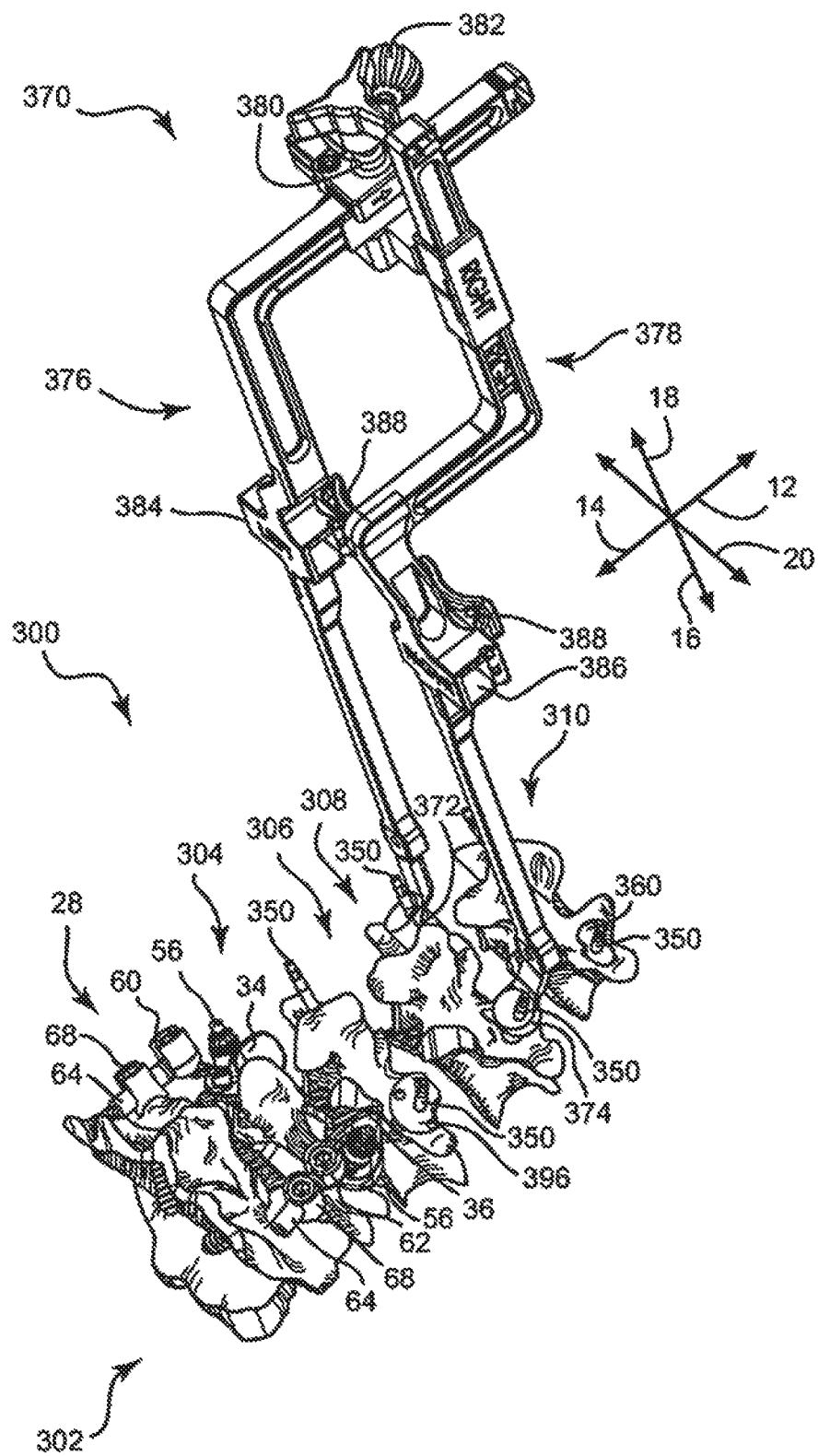
FIG. 14 is a perspective view of the portion of the spine of FIG. 8 with the frame registered on the fourth vertebra to facilitate formation of shaped resections on the saddle points of the third vertebra.

Referring to FIG. 14, a perspective view illustrates the portion of the spine 300 of FIG. 8 with the frame 370 registered on the fourth vertebra 308 to facilitate formation of shaped resections 396 on the saddle points of the third vertebra 306. As shown, the frame 370 is seated on the fourth vertebra 308 such that the anchors 372, 374 rest on the semispherical resections 358. The frame 370 is used in substantially the same manner set forth in the description of FIG. 12, except that the shaped resections 396 are formed on the saddle points of the third vertebra 306 instead of those of the second vertebra 304.

Thus, the third vertebra 306 is prepared to receive the superior prostheses 44, 46. After the shaped resections 396 have been formed, the superior prostheses 44, 46 of the cephalad facet joint assembly 26 and the inferior prostheses 38, 40 of the caudal facet joint assembly 24 may be secured to the third vertebra 306.

Figure 15:
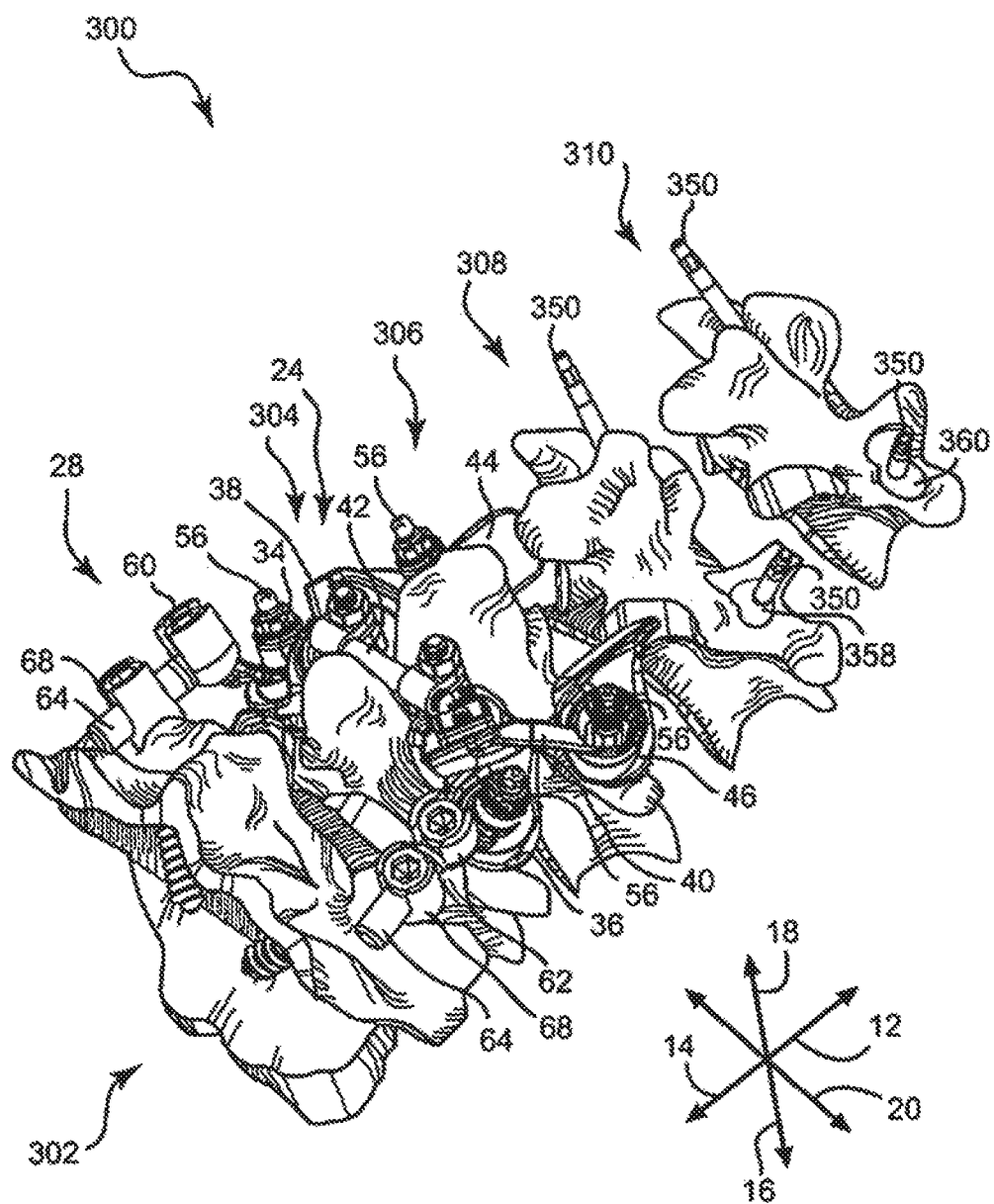
FIG. 15 is a perspective view of the portion of the spine of FIG. 8 after further attachment of the inferior prostheses of the caudal facet joint assembly and the superior prostheses of the cephalad facet joint assembly of the system of FIG. 1 to the portion of the spine.

Referring to FIG. 15, a perspective view illustrates the portion of the spine 300 of FIG. 8 after further attachment of the inferior prostheses 38, 40 of the caudal facet joint assembly 24, the crosslink assembly 42, and the superior prostheses 44, 46 of the cephalad facet joint assembly 26 of the system 10 of FIG. 1 to the portion of the spine 300. More precisely, the guide wires 350 are removed and the pedicle screws 54 are implanted in the pedicles 316 of the third vertebra 306, along the bores that remain after removal of the guide wires 350. The superior prostheses 44, 46 are positioned on the third vertebra 306 such that the fingers of the bone apposition surfaces 90 engage the small holes of the shaped resections 396.

The inferior prostheses 38, 40 of the caudal facet joint assembly 24 are then positioned such that the semispherical engagement surfaces 100 of the inferior prostheses 38, 40 rest within the semispherical receiving surfaces 92 of the superior prostheses 44, 46. The inferior prostheses 38, 40 remain polyaxially rotatable relative to the superior prostheses 44, 46.

The crosslink assembly 42 may then be loosely coupled to the inferior prostheses 38, 40. If desired, the crosslink assembly 42 may be loosely assembled before it is coupled to the inferior prostheses 38, 40. More precisely, the bolts 112 may be inserted through the implant coupling components 110 and the rod coupling components 114, and the nuts 116 may be loosely threaded onto the bolts 112. The ends of the rod 118 may be inserted into the rod coupling components. Then, the loosely assembled crosslink assembly 42 may be positioned and the implant coupling components 110 may be coupled to the inferior prostheses 38, 40.

The crosslink assembly 42 has not yet been tightened, and is therefore relatively freely configurable. Thus, the inferior prostheses 38, 40 may be rotated, with the crosslink assembly 42 coupled thereto, such that their articulation surfaces 104 are positioned to articulate optimally with the articulation surfaces 94 of the superior prostheses 34, 36 of the caudal facet joint assembly 24. Once the articulation surfaces 104 have reached the proper positions, the nuts 116 may be tightened on the bolts 112 to lock the configuration of the crosslink assembly 42, thereby providing a rigid bridge between the inferior prostheses 38, 40.

Then, the locking assemblies 56 may be used to restrict further rotation or translation of the inferior prostheses 38, 40 and the superior prostheses 44, 46, as described previously, in connection with FIG. 13. Thus, the prostheses 38, 40, 44, 46 and the crosslink assembly 42 are rigidly and securely attached to the third vertebra 306. The saddle points of the fourth vertebra 308 may then be further resected to prepare the fourth vertebra 308 to receive the inferior prostheses 72, 74 and the inferior prostheses 48, 50 of the cephalad facet joint assembly 26.

Figure 16:
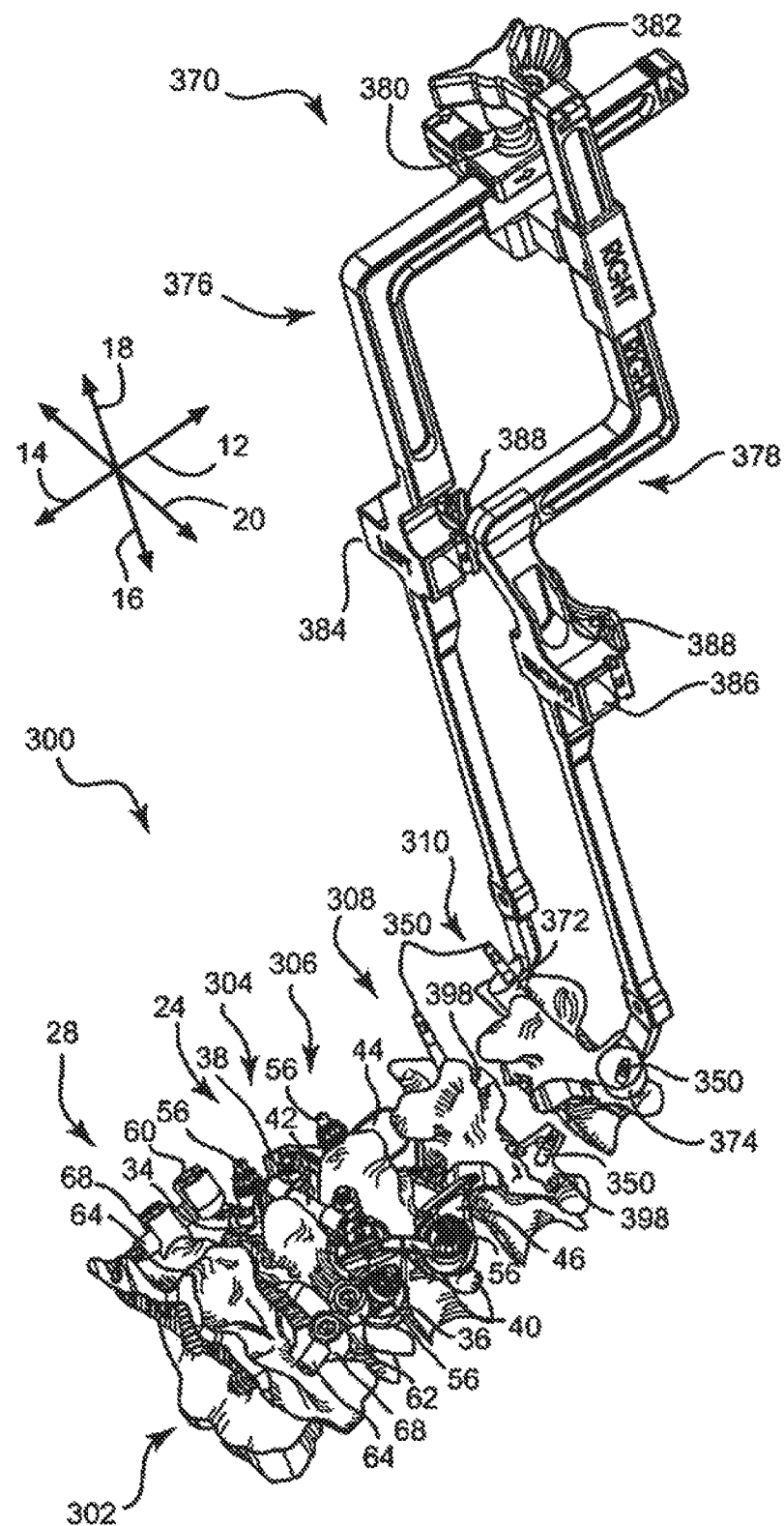
FIG. 16 is a perspective view of the portion of the spine of FIG. 8 with the frame registered on the fifth vertebra to facilitate formation of shaped resections on the saddle points of the fourth vertebra.

Referring to FIG. 16, a perspective view illustrates the portion of the spine 300 of FIG. 8 with the frame 370 registered on the fifth vertebra 310 to facilitate formation of shaped resections 398 on the saddle points of the fourth vertebra 308. As shown, the frame 370 is seated on the fifth vertebra 310 such that the anchors 372, 374 rest on the semispherical resections 360. The frame 370 is used in substantially the same manner set forth in the description of FIG. 12, except that the shaped resections 398 are formed on the saddle points of the fourth vertebra 308 instead of those of the second vertebra 304.

Thus, the fourth vertebra 308 is prepared to receive the inferior prostheses 72, 74. After the shaped resections 398 have been formed, the inferior prostheses 72, 74 and the inferior prostheses 48, 50 of the cephalad facet joint assembly 26 may be secured to the fourth vertebra 308.

Figure 17:
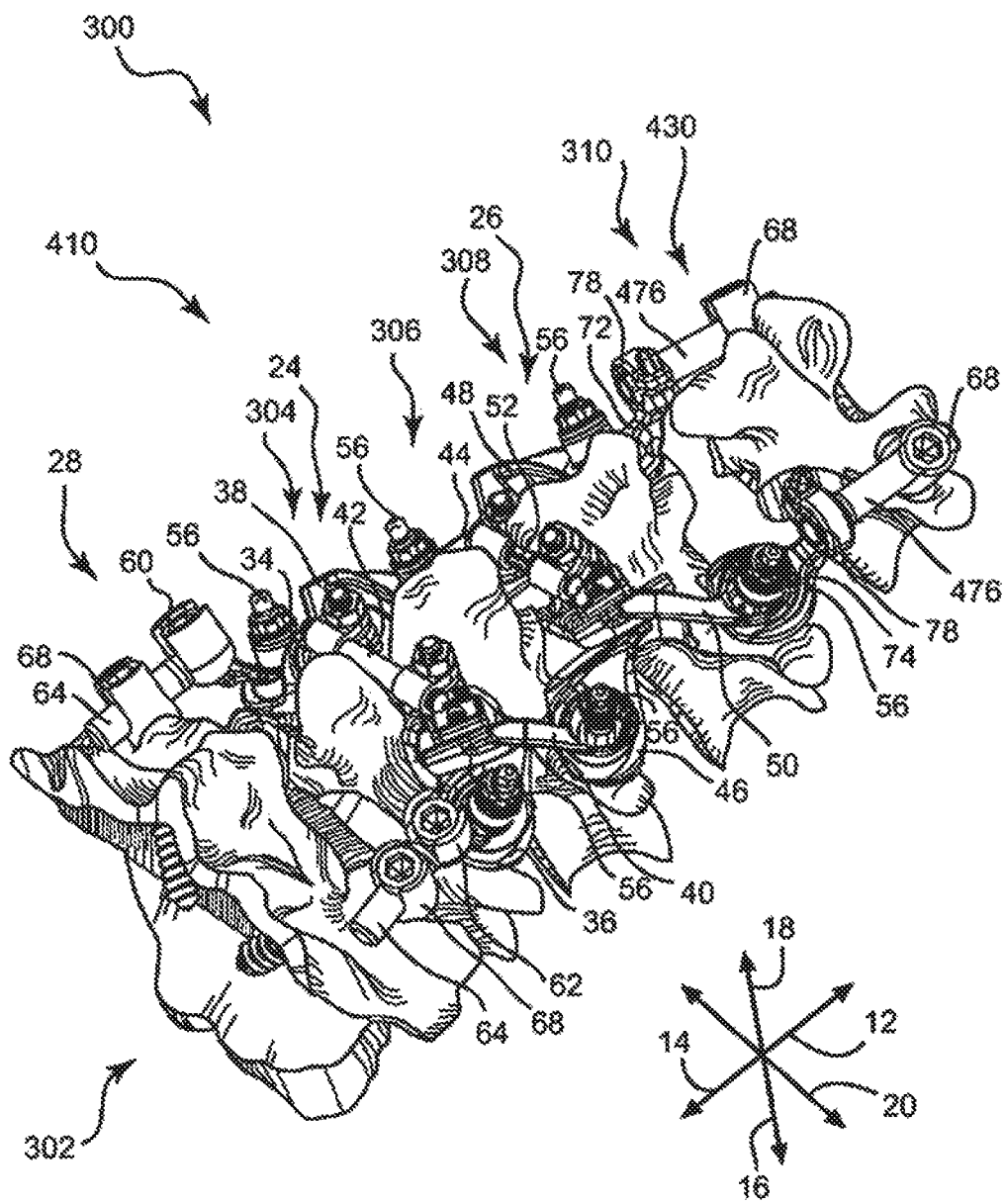
FIG. 17 is a perspective view of the portion of the spine of FIG. 8 after further attachment of the inferior prostheses of the cephalad facet joint assembly of FIG. 1 and a cephalad fusion assembly to the portion of the spine.

Referring to FIG. 17, a perspective view illustrates the portion of the spine 300 of FIG. 8 after further attachment of the inferior prostheses 72, 74 and the inferior prostheses 48, 50 of the cephalad facet joint assembly 26 to the portion of the spine 300. As shown, a complete system 410 has been attached to the vertebrae 302, 304, 306, 308, 310. The system 410 is similar to the system 10 of FIG. 1, except that the system 410 fuses only one, and not two, levels cephalad to the cephalad facet joint assembly 26. Accordingly, in place of the cephalad fusion assembly 30 of FIG. 1, the system 410 has a cephalad fusion assembly 430 that provides fusion for just one motion segment. Thus, cephalad fusion assembly 430 has rods 476 that may be somewhat shorter than the rods 76 of the cephalad fusion assembly 30 of FIG. 1.

In order to implant the remainder of the system 410, the guide wires 350 are first removed from the pedicles 318 of the fourth vertebra 308 and the pedicle screws 54 are implanted in the pedicles 318 of the fourth vertebra 308, along the bores that remain after removal of the guide wires 350. The inferior prostheses 72, 74 are positioned on the fourth vertebra 308 such that the fingers of the bone apposition surfaces 180 engage the small holes of the shaped resections 398.

The inferior prostheses 48, 50 of the cephalad facet joint assembly 26 are then positioned such that the semispherical engagement surfaces 100 of the inferior prostheses 48, 50 rest within the semispherical receiving surfaces 182 of the inferior prostheses 72, 74. The inferior prostheses 48, 50 remain polyaxially rotatable relative to the inferior prostheses 72, 74.

The crosslink assembly 52 may then be loosely coupled to the inferior prostheses 48, 50. If desired, the crosslink assembly 52 may be loosely assembled before it is coupled to the inferior prostheses 48, 50. More precisely, the procedure set forth in the description of FIG. 15, for assembly of the crosslink assembly 42, may also be used for the crosslink assembly 52.

The inferior prostheses 48, 50 may be rotated, with the crosslink assembly 52 coupled thereto, such that their articulation surfaces 104 are positioned to articulate optimally with the articulation surfaces 94 of the superior prostheses 44, 46 of the cephalad facet joint assembly 26. Once the articulation surfaces 104 have reached the proper positions, the crosslink 52 may be tightened to provide a rigid bridge between the inferior prostheses 48, 50.

Then, the locking assemblies 56 may be used to restrict further rotation or translation of the inferior prostheses 48, 50 and the inferior prostheses 72, 74, as described previously, in connection with FIG. 13. Thus, the prostheses 48, 50, 72, 74 and the crosslink assembly 52 are rigidly and securely attached to the fourth vertebra 308.

The pedicle screws 66 are implanted in the pedicles 320 of the fifth vertebra 310. This may be accomplished by removing the guide wires 350 and inserting the distal ends 160 of the pedicle screws 66 into the pedicles 320 through the bores left by removal of the guide wires 350. The pedicle screws 66 are implanted with the yoke assemblies 68 in place on the proximal ends 158 of the pedicle screws 66.

The polyaxial rod connectors 78 may be installed in the semispherical bores of the polyaxial receivers 184 of the inferior prostheses 72, 74 by the manufacturer of the system 410, or by the surgeon. Thus, if the polyaxial rod connectors 78 are not already in the semispherical bores of the polyaxial receivers 184, they may now be inserted therein. The caudal ends of the rods 476 may be inserted into the bores of the polyaxial rod connectors 78. The polyaxial rod connectors 78 swivel within the polyaxial receivers 184 such that the cephalad ends of the rods 476 can be placed in the troughs 166 of the yoke assemblies 68.

The yoke assemblies 68 are also polyaxially rotatable relative to the pedicle screws 66, and may thus be reoriented to receive the cephalad ends of the rods 476 at the optimal angles. Once the cephalad ends have been placed in the troughs 166 of the optimally-oriented yoke assemblies 68, the nuts 168 may be rotated into engagement with the walls 162, 164 of the yoke assemblies 68 and tightened to secure the cephalad ends of the rods 476 to the yoke assemblies 68, and to restrict further rotation of the yoke assemblies 68 relative to the pedicle screws. The receiver fasteners 186 may also be tightened to restrict further rotation of the polyaxial rod connectors 78 and the caudal ends of the rods 476 relative to the inferior prostheses 72, 74.

Facet joint replacement for the joints between the second and third vertebrae 304, 306 and between the third and fourth vertebrae 306, 308 is now complete. Additionally, fusion of the joint between the fourth and fifth vertebrae 308, 310 and fusion of the joint between the first and second vertebrae 302, 304 have also been completed. Thus, implantation of the system 410 is complete, and the surgical wound site may be closed.

Figure 18:
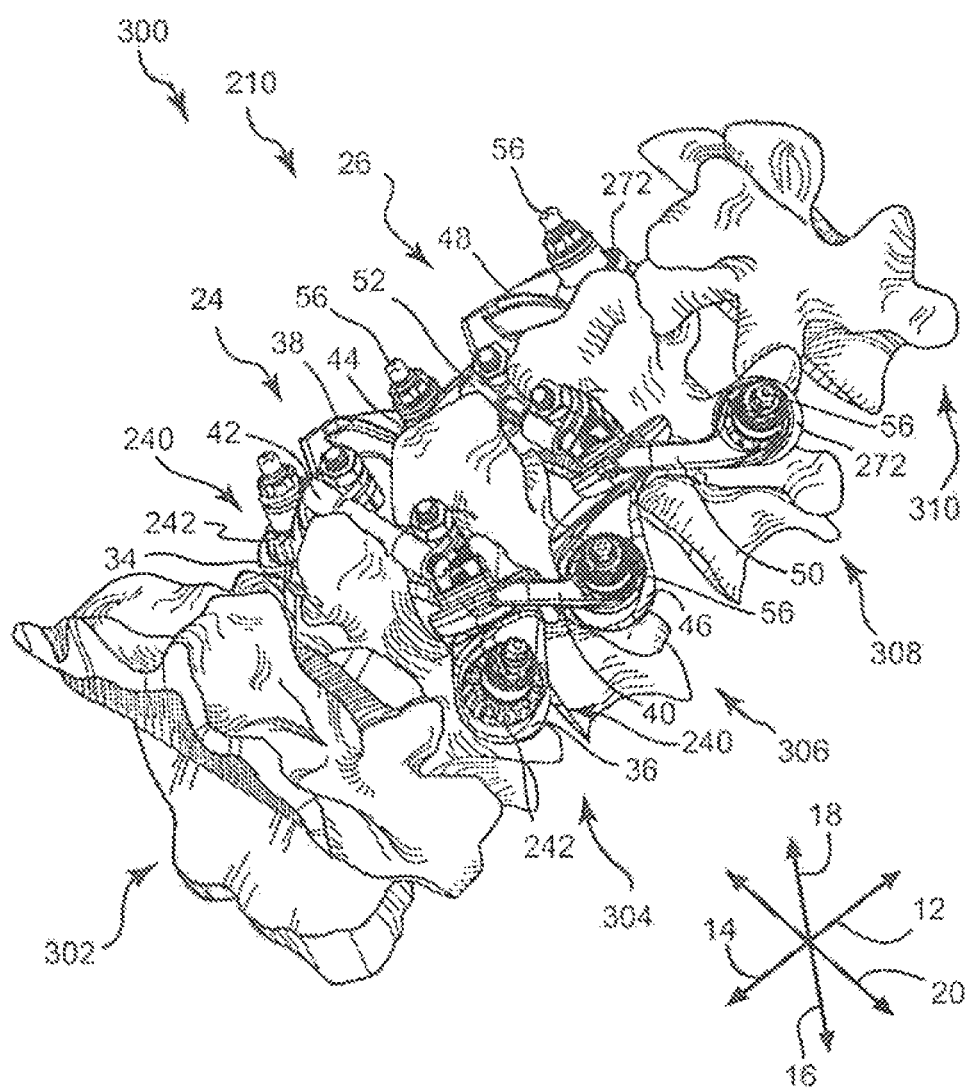
FIG. 18 is a perspective view of the portion of the spine of FIG. 8 with the system of FIG. 5 attached thereto instead of the system of FIG. 17.

Referring to FIG. 18, a perspective view illustrates the portion of the spine 300 of FIG. 8 with the system 210 of FIG. 5 attached thereto instead of the system 410 of FIG. 17. As in FIG. 5, the fusion assemblies 28, 30 have been omitted, and the engagement members 242 and in-growth cups 272 of FIGS. 6 and 7, respectively, have been included to compensate for the omission.

Accordingly, the caudal and cephalad facet joint assemblies 24, 26 have been secured to the second, third, and fourth vertebrae 304, 306, 308 to provide facet joint replacement for the joints between the second and third vertebrae 304, 306 and between the third and fourth vertebrae 306, 308. No fusion has been carried out. Thus, natural articulation may continue in the joint between the fourth and fifth vertebrae 308, 310 and in the joint between the first and second vertebrae 302, 304. Those of skill in the art will appreciate that the systems 10, 210, 410 are merely exemplary, and that many different systems may be envisioned with the aid of the present disclosure, incorporating facet joint replacement of one or more motion segments with or without fusion.

In addition to the surgical flexibility provided by the present invention, the present invention also opens new possibilities for revision. For example, the system 210 of FIG. 18 may be revised to provide caudal and/or cephalad adjacent-level fusion by removing the engagement members 242 and/or the in-growth cups 272, and replacing them with the caudal fusion assembly 28 and the split spheres 142 and/or with one of the cephalad fusion assemblies 30, 430.

Furthermore, facet joint replacement hardware such as the facet joint assemblies 24, 26 may be used to replace existing fusion assemblies such as the fusion assemblies 28, 30, or fusion assemblies currently in use in orthopedics. Similarly, facet joint replacement assemblies 24, 26 may be replaced with fusion hardware such as the fusion assemblies 28, 30. Additional levels of fusion or facet joint replacement may be added to a system of any configuration according to the invention. Advantageously, the pedicle screws 54 and 66 do not require bone cement, and may thus be relatively freely removable from the vertebrae 302, 304, 306, 308, 310 in the event that a reversal of a facet joint replacement or fusion procedure is desired.

The present invention may be embodied in other specific forms without departing from its spirit or essential characteristics. It is appreciated that various features of the systems and methods described above can be mixed and matched to form a variety of other alternatives. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for treating a patient comprising:
   a frame configured to extend across a midline of a spine to assist in the implantation of one or more fusion assemblies or prosthetic assemblies, wherein at least a portion of the frame is extendable external to the patient;
   a fusion assembly comprising a first yoke assembly and a first pedicle screw, wherein the yoke assembly is capable of polyaxial movement relative to the first pedicle screw, wherein the pedicle screw includes a head portion and a shaft portion extending therefrom for inserting into a bone member, the fusion assembly further comprising a rod that extends through the yoke assembly and a second yoke assembly operably connected to the rod, and
   a prosthetic assembly comprising a second pedicle screw and a receiving surface attached to the second pedicle screw, wherein the prosthetic assembly is capable of articular movement,
   wherein the frame includes a first arm, a second arm, a locking mechanism and an external anchoring mechanism,
   wherein frame permits translation between the first and second arms along three perpendicular axes.

2. The system of claim 1, wherein the fusion assembly comprises a semispherical engagement surface.

3. The system of claim 2, wherein the semispherical engagement surface of the fusion assembly is nested in the receiving surface of the prosthetic assembly.

4. The system of claim 3, further comprising a locking assembly received on the second pedicle screw above the semispherical engagement surface and the receiving surface.

5. The system of claim 4, wherein the locking assembly comprises a rotational locking member and a translational locking member.

6. The system of claim 1, wherein the receiving surface of the prosthetic assembly is attached to a first articulation surface configured to articulate with a second articulation surface of an adjacent prosthetic assembly.

7. The system of claim 1, wherein the prosthetic assembly comprises a facet joint assembly.

8. The system of claim 1, wherein the fusion assembly further comprises a nut designed to tighten the rod therein.

9. The system of claim 1, wherein the receiving surface of the prosthetic assembly comprises a concave, semispherical shape.

10. A system for treating a patient comprising:
a frame configured to extend across a midline of a spine to assist in the implantation of one or more fusion assemblies or prosthetic assemblies, wherein at least a portion of the frame is extendable external to the patient;
a fusion assembly comprising a first yoke assembly and a second yoke assembly connected via a rod, wherein the second yoke assembly includes an engagement surface attached thereto, and
a prosthetic assembly comprising a receiving surface, wherein the prosthetic assembly is capable of articular movement,
wherein the frame includes a first arm, a second arm, a locking mechanism and an external anchoring mechanism,
wherein frame permits translation between the first and second arms along three perpendicular axes.

11. The system of claim 10, wherein the fusion assembly is extendable across a first vertebral level and the prosthetic assembly is extendable across a second vertebral level.

12. The system of claim 10, wherein the receiving surface of the prosthetic assembly extends around a pedicle screw.

13. The system of claim 12, wherein the prosthetic assembly further comprises an articulation surface attached to the receiving surface.

14. The system of claim 13, wherein the prosthetic assembly further comprises a bone apposition surface.

15. The system of claim 14, wherein the prosthetic assembly further comprises a split sphere received in the receiving surface.

16. The system of claim 15, wherein the prosthetic assembly further comprises a locking member.

17. A system for treating a patient comprising:
a frame configured to extend across a midline of a spine to assist in the implantation of one or more fusion assemblies or prosthetic assemblies, wherein at least a portion of the frame is extendable external to the patient;
a first fusion assembly comprising a first yoke assembly and a first pedicle screw, wherein the first fusion assembly is extendable across a first vertebral level,
a prosthetic assembly capable of articular movement, wherein the prosthetic assembly is extendable across a second vertebral level, and
a second fusion assembly comprising a second yoke assembly a second pedicle screw, wherein the second fusion assembly is extendable across a third vertebral level,
wherein the frame includes a first arm, a second arm, a locking mechanism and an external anchoring mechanism,
wherein frame permits translation between the first and second arms along three perpendicular axes.

18. The system of claim 17, wherein at least a portion of the first fusion assembly nests within the prosthetic assembly.

19. The system of claim 18, wherein the prosthetic assembly comprises a facet joint assembly.

20. The system of claim 17, wherein the first fusion assembly and the second fusion assembly provide fixation, while the prosthetic assembly provides movement.

* * * * *